US007888458B1

(12) United States Patent
Harley et al.

(10) Patent No.: US 7,888,458 B1
(45) Date of Patent: Feb. 15, 2011

(54) DIAGNOSTICS AND THERAPY OF EPSTEIN-BARR VIRUS IN AUTOIMMUNE DISORDERS

(75) Inventors: John B. Harley, 439 NW. 20th St., Oklahoma City, OK (US) 73103; Judith A. James, 4436 NW. 36th St., No. 11, Oklahoma City, OK (US) 73112

(73) Assignees: John B. Harley, Cincinnati, OH (US); Judith A. James, Oklahoma, OK (US)

( * ) Notice: Subject to any disclaimer, the term of this patent is extended or adjusted under 35 U.S.C. 154(b) by 1484 days.

(21) Appl. No.: 08/781,296

(22) Filed: Jan. 13, 1997

Related U.S. Application Data

(63) Continuation-in-part of application No. 08/160,604, filed on Nov. 30, 1993, now Pat. No. 6,232,522.

(60) Provisional application No. 60/019,053, filed on May 16, 1996.

(51) Int. Cl.
*A61K 38/00* (2006.01)
*A61K 39/00* (2006.01)
*A61K 39/395* (2006.01)
*G01N 33/53* (2006.01)

(52) U.S. Cl. ............... 530/300; 424/130.1; 424/184.1; 435/7.1

(58) Field of Classification Search ............... 530/300, 530/326, 350, 826, 806; 424/184.1, 186.1, 424/206.1, 230.1
See application file for complete search history.

(56) References Cited

U.S. PATENT DOCUMENTS

| 4,654,419 | A | * | 3/1987 | Vaughan ............ 530/326 |
| 4,707,358 | A | * | 11/1987 | Kieff ............... 424/89 |
| 5,637,454 | A | * | 6/1997 | Harley .............. 435/5 |
| 5,679,774 | A | * | 10/1997 | Wolf ............... 530/350 |
| 5,723,283 | A | * | 3/1998 | Classen ............. 435/4 |
| 5,726,286 | A | * | 3/1998 | Alderson ........... 530/300 |
| 5,874,531 | A | * | 2/1999 | Strominger ......... 530/326 |
| 5,965,353 | A | * | 10/1999 | Middeldorp ........ 435/5 |

FOREIGN PATENT DOCUMENTS

| WO | WO 86/01210 | | 2/1986 |
| WO | WO 88/09932 | | 6/1988 |
| WO | WO 91/11718 | A1 | 8/1991 |
| WO | WO 91/18920 | | 12/1991 |
| WO | 94/06912 | * | 3/1994 |
| WO | WO 94/06912 | * | 3/1994 |

OTHER PUBLICATIONS

Van Regenmortel, M.H.V. Vaccine, vol. 19:2369-2374.*
Ebihara et al. (Nippon Kagaku Zasshi (1969) vol. 90, No. 8, pp. 819-823).*
Stuber et al. (International Immunology (1995) vol. 7, No. 4, pp. 653-663).*
Chen et al. (Virology (1994) vol. 205, pp. 486-495).*
Stuber et al. (European Journal of Immunology (1992) vol. 22, pp. 2697-2703).*
Russell et al. Journal of Molecular Biology (1994) vol. 244, pp. 332-350.*
Rhodes, et al. "Human Immune responses to Synthetic Peptides from the Epstein-Barr Nuclear Antigen," *J. Immunol*, 134-211-216 (1985).
Baraket, et al., "IgG Antibodies From Patients with Primary Sjogren's Syndrome and systemic Lupus Erythematosus Recognize Different Epitopes in 60-kD SSA/Ro Protein," *Clin. Exp. Immunol.* 89:38-45(1992).
Ben-Chetrit, et al., "Isolation and Characterization of a cDNA Encoding the 60-kD Component of the Human SSA/Ro Ribonucleoprotein Autoantigen," *J. Clin. Inv.* 83:1284-1292 (1997).
Chambers, et al., "Isolation and analysis of cDNA Clones Expressing Human Lupus La Antigen," *Proc. Natl. Acad. Sci. USA* 82:2115-2119 (1985).
Chan, et al., "Ribonucleoprotein SS-B/La belongs to a Protein Family with Consensus Sequences for RNA Binding," *Nucl. Acids Res.* 17:2233-2244 (1989).
Dickey, "Human Autoantibody Producing Grafts in SCID Mice," presented to the Oklahoma Lups Association, Inc., Sep. 1, 1989.
Elkon, et al., "Epitope Mapping of Recombinant HeLa SmB and B' Peptides Obtained by the Polymerase Chain Reaction," *J. of Immun.* 145:636-643 (1990).
Hardgrave, et al, "Antibodies to Vesicular Stomatitis Virus Proteins in Patients with Systemic Lupus Erythematosus and in Normal Subjects," *Arthritis and Rheumatism* 36(7):962-970 (1993).
Kaufman, et al., "In Vivo Binding of Gram-Negative Bacterial Peptides to Hla-B27: A Possible Relationship to Anklosing Spondylitis Pathogenesis", *Arthritis Rheum* 39:S298 (1996).
McAllister, et al., "cDNA Sequence of the rat U snRNP-associated Protein N: Description of a Potential Sm Epitope," *EMBO J.* 8:1177-1181 (1989).
Schaack, "Molecular Mimicry in HLA-B-27-Related Arthritis," *Annals of Internal Medicine* 111(7):581-591 (1989).

(Continued)

*Primary Examiner*—Lori A Clow

(57) ABSTRACT

Data consistent with autoimmune disease being caused by Epstein-Barr virus are shown. Based on this evidence, an effective vaccine would prevent the autoimmune disease in those vaccinated, modified or administered so that the vaccine is not itself capable of inducing autoimmune disease. In the case of anti-Sm, structures to be avoided in an Epstein-Barr virus-derived vaccine have been identified. Differences have been identified in the immune responses to Epstein-Barr infection between individuals who develop a specific autoimmune disease and those who do not. These differences are used to distinguish those who are at greater risk for developing specific autoimmune diseases from those who are a lesser risk. Assuming Epstein-Barr virus causes autoimmune disease and that Epstein-Barr virus remains latent in the patient for life, reactivation of the virus from the latent state is important in generating or maintaining the autoimmune response that culminates in autoimmune disease. Cells infected with latent virus may also encourage autoimmunity. Based on the understanding that reactivation or latency are important to produce or sustain autoimmunity, then therapies directed against Epstein-Barr virus will also be effective therapies for the autoimmune manifestations of disease for which Epstein-Barr virus is responsible.

13 Claims, 11 Drawing Sheets

OTHER PUBLICATIONS

Sharpe, et al., "Isolation of cDNA Clones Encoding the Human Sm B/B' Auto-Immune Antigen and Specifically Reaching with Human Anti-Sm Auto-", *FEBS Lett.* 250:585-590 (1989).

Sturgess, et al., "Characteristics and Epitope Mapping of a Cloned Human Autoantigen La," *J. Immun.* 3212-3218 (1988).

Yamamoto, et al., "Isolation and Characterization of a Complementary DNA Expressing Human U1 Small Nuclear Ribonucleoprotein C Polypeptide," *J. Immun.* 140:311-317 (1988).

*The Medical Letter on Drugs and Therapeutics* 37(951):55-57 (1995).

* cited by examiner

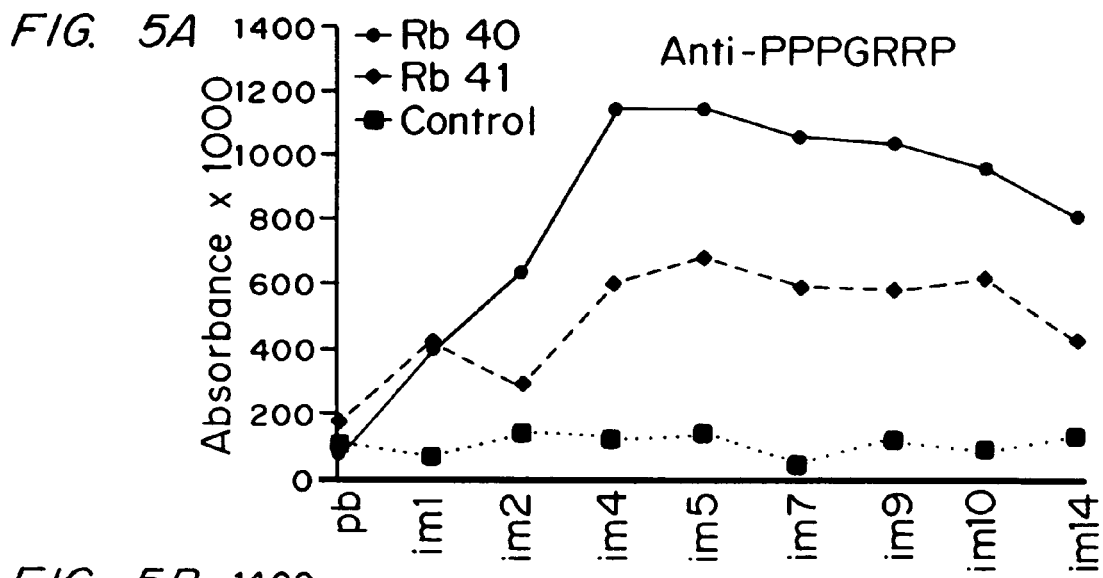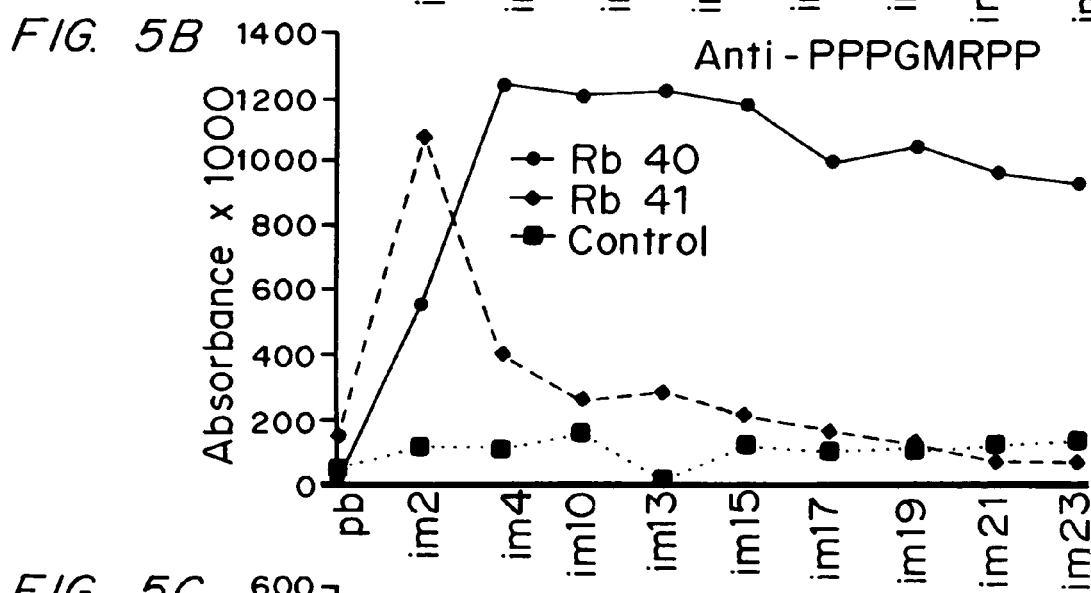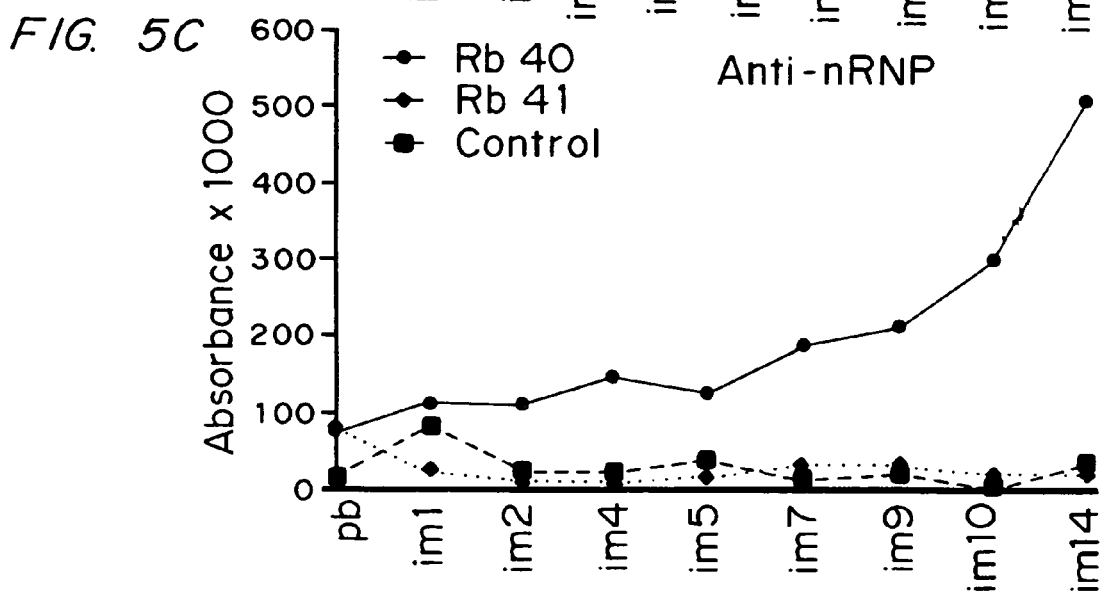

```
                           SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:1:

Pro Pro Pro Gly Arg Arg Pro
    1               5

(2) INFORMATION FOR SEQ ID NO:2:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:2:

Gly Arg Gly Arg Gly Arg Gly Gly
    1               5

(2) INFORMATION FOR SEQ ID NO:3:

(i) SEQUENCE CHARACTERISTICS:
              (A) LENGTH: 7 amino acids
              (B) TYPE: amino acid
              (C) STRANDEDNESS: single
              (D) TOPOLOGY: linear (ii) MOLECULE TYPE: protein (iii) HYPOTHETICAL: NO
```

```
        (iv) ANTI-SENSE: NO (xi) SEQUENCE DESCRIPTION: SEQ ID NO:3:

Arg Gly Arg Gly Arg Glu Lys
1               5

(2) INFORMATION FOR SEQ ID NO:4:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:4:

Pro Pro Pro Gly Met Arg Pro Pro
1               5

(2) INFORMATION FOR SEQ ID NO:5:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:5:

Pro Pro Pro Gly Ile Arg Gly Pro
1               5

(2) INFORMATION FOR SEQ ID NO:6:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:6:

Pro Ala Pro Gly Met Arg Pro Pro
1               5

(2) INFORMATION FOR SEQ ID NO:7:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: protein (iii) HYPOTHETICAL: NO
```

(iv) ANTI-SENSE: NO (xi) SEQUENCE DESCRIPTION: SEQ ID NO:7:

Gly Ala Gly Ala Gly Ala Gly Ala Gly Ala Gly Ala Gly Ala Gly Ala
1               5                   10                  15

Gly Ala Gly Ala Gly Ala Gly Ala
            20

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:8:

Pro Pro Pro Gly Met Arg Gly Pro
1               5

(2) INFORMATION FOR SEQ ID NO:9:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:9:

Gly Arg Gly Arg Gly Arg Gly Arg Gly Arg Gly Arg Gly Arg Gly Arg
1               5                   10                  15

Gly Arg Gly Arg Gly Gly Pro Arg Arg Arg
            20                  25

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:10:

CCAGAGGTAA GTGGACTT                                                 18

(2) INFORMATION FOR SEQ ID NO:11:

(i) SEQUENCE CHARACTERISTICS:
            (A) LENGTH: 18 base pairs
            (B) TYPE: nucleic acid -continued (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:11:

GACCGGTGCC TTCTTAGG                                                     18

(2) INFORMATION FOR SEQ ID NO:12:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:12:

AAGACGATTC GGGTTGTGAG GTGGTGTGGG TCCGTGTGTG ATGTGTGTGG GTGGGCAG        58

(2) INFORMATION FOR SEQ ID NO:13:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:13:

Gly Pro Gln Arg Arg Gly Gly Asp Asn His Gly Arg Gly Arg Gly Arg
1               5                   10                  15

Gly Arg Gly Arg Gly Gly Arg Pro Gly
            20                  25

(2) INFORMATION FOR SEQ ID NO:14:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:14:

Gly Gly Ser Gly Ser Gly Pro Arg His Arg Asp Gly Val Arg Arg Pro
1               5                   10                  15

Gln Lys Arg Pro
            20

```
(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:15:

Arg Pro Gln Lys Arg Pro Ser Cys
1               5

(2) INFORMATION FOR SEQ ID NO:16:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:16:

Gln Lys Arg Pro Ser Cys Ile Gly Cys Lys Gly Thr His Gly Gly Thr
1               5                   10                  15
Gly (2) INFORMATION FOR SEQ ID NO:17:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:17:

Gly Thr Gly Ala Gly Ala Gly Ala Arg Gly Arg Gly Gly
1               5                   10

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:18:

Ser Gly Gly Arg Gly Arg Gly Gly
```

```
1               5
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:19:

```
Arg Gly Gly Ser Gly Gly Arg Arg Gly Arg Gly Arg
1               5                   10
```

(2) INFORMATION FOR SEQ ID NO:20:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:20:

```
Arg Ala Arg Gly Arg Gly Arg Gly Arg Gly Glu Lys Arg Pro Arg Ser
1               5                   10                  15
```

(2) INFORMATION FOR SEQ ID NO:21:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:21:

```
Ser Ser Ser Ser Gly Ser Pro Pro Arg Arg Pro Pro Gly Arg
1               5                   10                  15
```

(2) INFORMATION FOR SEQ ID NO:22:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:22:

```
Arg Pro Pro Pro Gly Arg Arg Pro Phe Phe His Pro Val Gly Glu Ala
1               5                   10                  15

Asp Tyr Phe Glu Tyr His Gln Glu Gly
                20              25
```

(2) INFORMATION FOR SEQ ID NO:23:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:23:

```
Pro Asp Val Pro Pro Gly Ala Ile
1               5
```

(2) INFORMATION FOR SEQ ID NO:24:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:24:

```
Pro Gly Ala Ile Glu Gln Gly Pro Ala
1               5
```

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:25:

```
Gly Pro Ser Thr Gly Pro Arg Gly
1               5
```

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:26:

Gly Gln Gly Asp Gly Gly Arg Arg Lys
1               5

(2) INFORMATION FOR SEQ ID NO:27:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:27:

Asp Gly Gly Arg Arg Lys Lys Gly Gly Trp Phe Gly Lys His Arg
1               5                   10                  15

(2) INFORMATION FOR SEQ ID NO:28:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:28:

Gly Lys His Arg Gly Gln Gly Gly Ser Asn
1               5                   10

(2) INFORMATION FOR SEQ ID NO:29:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:29:

Gly Gln Gly Gly Ser Asn Pro Lys
1               5

(2) INFORMATION FOR SEQ ID NO:30:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:30:

Asn Pro Lys Phe Glu Asn Ile Ala
1               5

(2) INFORMATION FOR SEQ ID NO:31:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:31:

Arg Ser His Val Glu Arg Thr Thr
1               5

(2) INFORMATION FOR SEQ ID NO:32:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:32:

Val Phe Val Tyr Gly Gly Ser Lys Thr
1               5

(2) INFORMATION FOR SEQ ID NO:33:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:33:

Gly Ser Lys Thr Ser Leu Tyr Asn Leu
1               5

(2) INFORMATION FOR SEQ ID NO:34:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:34:

Gly Met Ala Pro Gly Pro Gly Pro
1               5

(2) INFORMATION FOR SEQ ID NO:35:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:35:

Pro Gln Pro Gly Pro Leu Arg Glu
1               5

(2) INFORMATION FOR SEQ ID NO:36:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:36:

Cys Asn Ile Arg Val Thr Val Cys
1               5

(2) INFORMATION FOR SEQ ID NO:37:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:37:

Arg Val Thr Val Cys Ser Phe Asp Asp Gly
1               5                   10

(2) INFORMATION FOR SEQ ID NO:38:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein -continued

```
    (iii) HYPOTHETICAL: NO (iv) ANTI-SENSE: NO (xi) SEQUENCE DESCRIPTION: SEQ ID NO:38:

Pro Pro Trp Phe Pro Pro Met Val Glu Gly
1               5                   10
```

DIAGNOSTICS AND THERAPY OF EPSTEIN-BARR VIRUS IN AUTOIMMUNE DISORDERS

PRIORITY INFORMATION

This application claims the benefit of U.S. Ser. No. 60/019, 053 entitled "EBV Vaccine for Treatment or Prevention of SLE" filed May 16, 1996 by John B. Harley and is a continuation-in-part of U.S. Ser. No. 08/160,604 filed Nov. 30, 1993, now U.S. Pat. No. 6,232,522, entitled "Peptide Induction of Autoimmunity and Clinical Symptomology" by John B. Harley, Judith A. James, and R, Hal Scofield.

U.S. GOVERNMENT RIGHTS

The U.S. Federal Government has rights in this invention by virtue of Grant NO. RO1 AR42460 to John B. Harley and KO8 AR01981 to Judith A. James from the National Institutes of Health.

BACKGROUND OF THE INVENTION

This is in the area of the prevention, diagnosis, and treatment of autoimmune diseases having Epstein-Barr virus as an etiological agent.

Epstein-Barr virus infects B cells and induces a large number of different autoantibodies in the early phase of infection. The B cell proliferation and autoantibody production is eventually brought under control in nearly everyone by virus specific T cells. Thereafter, the virus remains latent, surviving in the host for the remainder of the natural life. Once the host is infected the virus continues to "reactivate" at a low level. Evidence for this reactivation is the shedding of virus in the oral cavity, infection through exchange of oral secretions, the spontaneous in vitro outgrowth of transformed B cells, and the spontaneous production of Epstein-Barr virus in vitro. The continuous presence of virus presents a significant challenge to the immune system and requires that the immune mechanisms sustain viral suppression over the many decades of remaining life. If Epstein-Barr virus causes autoimmune disease, then this feature, the sustained presence of a low level of virus in the host continuously emerging from latency, is likely to be important in diseases that appear long after the original infection by Epstein-Barr virus.

Epstein-Barr virus is a herpes virus and is also called Human Herpes Virus 4. This virus is from the genus *Lymphocryptovirus* and subfamily gammaherpesvirinae. This is the only gamma herpes virus known in man. There are several very good reviews of the biology and structure of Epstein-Barr virus. The reader is referred to classic reviews (Kieff, E. and Liebowitz, D.: Epstein-Barr virus and its replication. In Virology, 2nd ed. Fields et al., eds. pp 1889-1921 (Raven Press, New York 1990); Miller, G.: Epstein-Barr virus. ibid. pp. 1921-1958; Evans, A. S. and Niederman, J. C.: Epstein-Barr virus. In Viral Infections in Humans, 3rd ed. Evans, A. S. ed. pp 265-292 (Plenum, New York City 1989)). Like the other herpes viruses, this is a DNA virus and has a strong propensity for latency. Once latent this virus emerges from latency at a low level throughout life. Epstein-Barr virus induces lymphoma in some non-human primates. In man Epstein-Barr virus appears to be responsible for at least infectious mononucleosis, Burkitt's lymphoma and nasopharyngeal carcinoma.

Epstein-Barr virus infects the epithelium of the upper airway, B cells and a few T cells. On B cells the viral receptor is the Complement Receptor, Type 2, also known as the CR2 receptor. Infected B cells are able to present antigen, though the virus has recently been found to produce inhibitors of antigen processing (Levitskaya, J. *Nature* 375:685-688 (1995)), and to synthesize a molecule similar to Il-10 which has profound local effects (Suzuki, T. et al *J. Exp. Med.* 182:477-486 (1995)). Depending upon what genes are expressed, latently infected B cells may not respond to stimuli in the usual way and may not provide the signals, either qualitatively or quantitatively, that would otherwise be provided. Such aberrant influences upon the normal immune response may provide the basis for subsequent autoimmune disease in some people.

Epstein-Barr virus has been known for more than three decades. For the specific example of an autoimmune disease used herein to illustrate the principles of the invention, many others have considered a relationship between systemic lupus erythematosus and Epstein-Barr virus. The size of the separate literatures concerning lupus, on the one hand, and Epstein-Barr virus on the other are too vast to comprehensively review here. Nevertheless, over 25 years ago antibody titers were noted to be elevated against a number of viruses including rubella, measles, and parainfluenza 1 (Hollinger, F. B. et al. *Bact. Proc.* 131:174 (1970); Phillips, P. E. and Christian, C. L. *Science* 168:982-4 (1970); Hurd, E. R. et al. *Arthritis Rheum.* 13:724-33 (1970)). Perhaps, Dalldorf and colleagues were the first to report an evaluation of the titers of antibody against Epstein-Barr virus in lupus patients; they found no difference between lupus patients and normal controls (Dalldorf, G. et al. J. Am. Med. Assn. 208:1365-8 (1969)).

In contrast, Evans and colleagues claimed to find elevated titers of anti-Epstein-Barr antibodies relative to controls (Evans, A. S., et al. *Lancet* 1:167-168 (1970)). This paper generated a number of responses, all of which encouraged caution in interpreting these results or address the potential artifacts which could confuse the interpretation (Newell, G. R. and Stevens, D. A. *Lancet* 1:652 (1971); Evans, A. S. *Lancet* 1:1023-4 (1971); Gergely, L. et al. *Lancet* 1:325-326 (1973); Evans, A. S. and Rothfield, N. F. *Lancet* 1:1127-1128 (1973); Phillips, P. E. et al. *Lancet* 1:1449 (1973)). Much of the confusion arises from the use of immunofluorescence assays for the detection of anti-Epstein-Barr virus seroconversion. This investigative activity culminated in a remarkable study in which many participants of the controversy combined their resources to develop data they interpreted to show, "the combined approach used in this study fails to provide supportive evidence that E. B. virus is a causative agent in the connective-tissue diseases" (Klippel, J. H. et al. *Lancet* 2:1057-1058 (1973)). They found no difference in the titer of antibodies against Epstein-Barr virus in lupus compared to controls.

A Japanese group found a high frequency of antibodies against Epstein-Barr virus Nuclear Antigens 2 and 3 in lupus patient sera, compared to normal controls (Kitagawa, H., Et al. *Immunol. Lett.* 17:249-252 (1988)). Another Japanese group found higher levels of antibody directed against a membrane antigen from Epstein-Barr virus in lupus (and rheumatoid arthritis) sera than in controls (Yokochi, T. et al. *J. Rheumatol.* 16:1029-1032 (1989)). Similarly, an Australian group found a modest increase in antibodies against early antigens (Sculley, D. G., et al. *J. Gen. Virol.* 67:2253-2258 (1986)).

An Italian group has shown that the affinity purified antibodies from the 95-119 region of Sm D from lupus patients bind the Epstein-Barr virus Nuclear Antigen-1 between amino acids 35 and 58 (Sabbatini, A., et al. *Eur. J. Immunol.* 23:1146-1152 (1993)).

The most recent contribution to this question uses both molecular methods to detect Epstein-Barr DNA and serologic methods to detect antibodies (Tsai, Y. et al. *Int. Arch. Allergy Immunol.* 106:235-240 (1995)). This study also shows no significant differences between lupus patients and controls.

Other diseases, including both rheumatoid arthritis and Sjogren's syndrome, have been explored for a possible relationship to Epstein-Barr virus. Robert Fox and colleagues presented their conception of this area in 1992 (Fox R. I., Luppi, M. and Kang H. *J. Rheumatol.* 19:18-24 (1992)). The evidence which they conclude supports a role for Epstein-Barr virus in rheumatoid arthritis includes: similarity between synovial and viral antigens, higher levels of antibodies against the Epstein-Barr virus Nuclear Antigens 1 and 3, and the lower ability of lymphocytes to prevent the outgrowth of autologous, Epstein-Barr virus infected lymphocytes (Fox, R. I. *Current Opin. Rheum.* 7:409-416 (1995)). Others have found a small increase in the frequency of latency for Epstein-Barr virus in rheumatoid arthritis, but a much larger effect for Human Herpes virus-6 (Newkirk, M. M. et al. *Br. J. Rhuem.* 33:317-322 (1994)).

In Sjogren's syndrome Fox and colleagues note the higher level and frequency of Epstein-Barr virus in salivary gland epithelium and gland tissue (Fox, R. I. et al. *J. Immunol* 137:3162-3168 (1986)). Other viruses have also been considered by this author (Fox, R. I. *Current Opin. Rheum.* 7:409-416 (1995)).

Others have developed interesting data from Sjogren's syndrome. Pflugfelder and colleagues found evidence for Epstein-Barr virus in 80% of the lacrimal gland specimens from Sjogren's syndrome patients and in none of the controls (Pflugfelder, S. A. et al *Ophthalmology* 97:976-984 (1990); and Pflugfelder, S. A. et al. *Am. J. Pathol.* 143:49-64 (1993)). Karameris and colleagues found higher levels of hybridization between an Epstein-Barr virus DNA probe and the nuclei of salivary gland epithelial cells in Sjogren's syndrome than in controls (Karameris, A. et al. *Clin. Exp. Rheum.* 10:327-332 (1992)).

Others, however, found no such relationship and concluded that the frequency of Epstein-Barr virus DNA in salivary biopsy specimens was no different in patients with Sjogen's syndrome when compared with normals (Venables, P. J. W., et al. *Clin. Exp. Immunol.* 75:359-364 (1989); Venables, P. J. W., et al. *J. Autoimmunity* 2:439-438 (1989); Deacon, L. M., et al. *Am J. Med.* 92:453-454 (1992)). The data collected by Venables and colleagues were interpreted to show that there was "no evidence that the Epstein-Barr virus infection load is increased . . . [in Sjogren's syndrome]" (Venables, P. J. W. et al. *Clin. Exp. Immunol.* 75:359-364 (1989)), which is similar to the results of Maitland (Maitland, N. J. *Am. J. Med.* 96:97 (1994)). Venables and colleagues also refuted there being any abnormality in the serologic response of Sjogren's syndrome patients to Epstein-Barr virus (Deacon, E. M., et al. *J. Pathol.* 163:351-360 (1991)), citing their data as well as the negative serologic results of Mariette and colleagues (Mariette, X., et al. *Am. J. Med.* 90:286-294 (1991)).

A Japanese group found an increase in the Epstein-Barr virus production by B cells in patients with Sjogren's syndrome (Tateishi, M. et al. *Arthritis Rhuem.* 36:827-835 (1993)). Also, Inoue and colleagues found a minor increase in antibody levels against Epstein-Barr virus Nuclear Antigen-2 domains in Sjogren's syndrome compared to controls (Inoue, N. et al. *J. Infect. Dis.* 164;22-28 (1991)). Another Japanese group reported a modest elevation of anti-Epstein-Barr Nuclear antigen, anti-Early Antigen and anti-Epstein-Barr virus Viral Capsid Antigen (all measured by immunofluorescence) (Toda, I., et al. Sjogren's syndrome (SS) and Epstein-Barr virus (EBV) reactivation. In Lacrimal Gland, Tear Film, and Dry Eye Syndrome. D. A. Sullivan, ed. pp 647-650 (Plenum Press, New York 1994).

Nevertheless, Whittingham has proposed that Epstein-Barr virus is an etiologic agent for Sjogren's syndrome (Whittingham, S., et al. *Med. Hypothesis* 22:373-386 (1987)). She and her colleagues imagine that the Epstein-Barr viral RNAs called EBER 1 and EBER 2, which are known to bind the La autoantigen, facilitate overcoming tolerance to La and generating autoimmunity. They postulate that the combined effect of Epstein-Barr virus infection and autoimmunity leads to Sjogren's syndrome.

Morshed and colleagues published data showing an increased level of Epstein-Barr virus DNA in patients with primary biliary cirrhosis compared to controls from peripheral blood mononuclear cells, saliva, and fixed liver tissue (Morshed, S. A. et al. *Gastroenterol. Jpn.* 27:751-758 (1992)). The nuclear dot antigen is an autoantigen bound by autoantibody found in a few sera from patients with primary biliary cirrhosis. This autoantibody is also uncommonly found in lupus and rheumatoid arthritis sera. Analysis of the epitopes of the nuclear dot antigen has revealed two epitopes which have homology with Epstein-Barr virus protein sequences (Xie, K. and Snyder, M. *Proc. Natl. Acad. Sci.* 92:1639-1643 (1995)).

An example of double infection with Epstein-Barr virus and another virus is found in a cell line isolated from a patient with apparent multiple sclerosis (Haahr, S. et al. *Ann. N. Y. Acad. Sci.* 724:148-156 (1996)). The increased prevalence of seroconversion among multiple sclerosis patients, relative to controls, has led to the suggestion that Epstein-Barr virus may be an etiologic agent in multiple sclerosis (Sumaya, C. V. et al. *Ann. Neurol.* 17:371-377 (1985); Bray, P. F., et al. *Arch. Neurol.* 40:406-408 (1983); Larsen. P. D., et al. *Neurology* 35:435-438 (1985); Warner, H. B. and Carp. R. I. *Med. Hypothesis* 25:93-97 (1988); Bray, P. F. et al. *Neurology* (1992)).

Because of evidence implicating Epstein-Barr virus in infectious mononucleosis, B cell lymphoma (in immunocompromised hosts), burkitt's lymphoma, nasopharyngeal carcinoma, and some cases of Hodgkin's lymphoma, there has been some activity building toward a vaccine against Epstein-Barr virus (Morgan, A. J., et al. *J. Med. Virol.* 29:74-78 (1989); and Morgan, A. J. *Vaccine* 10:563-571 (1992)). Recombinant vectors expressing gp340/220 in a bovine papillomavirus vector or in an adenovirus vector protected five of six cottontop tamarins from lymphomas that otherwise occur after infection with Epstein-Barr virus (Finerty, S., et al. *J. Gen. Virol.* 73:449-453 (1992)). A subunit of the gp340/200 in alum protected three of five cotton top tamarins from lymphomas (Finerty, S., et al. *Vaccine* 12:1180-1184 (1994)), suggesting that this strategy might not be especially effective. A trial of an Epstein-Barr virus vaccine of gp340/220 in a Vaccinia virus vector has been reported from China and failed to protect a third of those immunized (Gu, S. et al. *Dev. Biol. Stand.* 84:171-177 (1995)).

A variety of therapies have been attempted against Epstein-Barr virus. These include inducing the lysis cycle in cells latently infected by virus (Gutierrez, M. I., et al. *Cancer Res.* 56:969-972 (1996)). Patients with the Epstein-Barr virus related lymphomatoid granulomatosis have been treated with interferon-alpha 2b with the preliminary impression that the treatment was successful (Wilson, W. H., et al. *Blood* 87:4531-4537 (1996)). Cycloheximide has been demonstrated to be useful in vitro (Ishii, H. H., et al. *Immunol. Cell Biol.* 73:463-468 (1995)). Therapy with a T cell line has been attempted (Kimura, H. et al. *Clin. Exp. Immunol.* 103:192-

298 (1996)), as has adoptive transfer of gene-modified virus-specific T lymphocytes (Heslop, H. E. et al. *Nature Med.* 2:551-555 (1996)). Data available do not appear to particularly support the use of acyclovir for Epstein-Barr virus infections (Wagstaff, A. J., et al. *Drugs* 47:153-205 (1994)), though FK506 (a relative of cyclosporine) may have some benefit (Singh, N., et al. *Digestive Dis. Sci.* 39:15-18 (1994)). Monoclonal antibodies have been used to treat the virus-induced lymphoproliferative syndrome (Lazarovots, A. I., et al. *Clin. Invest. Med.* 17:621-625 (1994)).

It is therefore an object of the present invention to provide strategies to prevent autoimmune disease by vaccination with vaccines based upon Epstein-Barr virus or upon the structure of Epstein-Barr virus.

It is a further object of this invention to provide vaccines based upon Epstein-Barr virus or upon the structure of Epstein-Barr virus which will have little risk of inducing autoimmune disease.

It is a further object of this invention to provide diagnostics which will identify people exposed to Epstein-Barr virus who are at an increased risk for autoimmune disease and, alternatively, those who are at decreased risk for developing autoimmune disease.

It is a further object of this invention to provide for the application of antiviral therapy directed against Epstein-Barr virus in the treatment of autoimmune disease.

It is a further object of this invention to provide diagnostics and therapeutics for autoimmune disease based upon the changes induced by the host by Epstein-Barr virus.

SUMMARY OF THE INVENTION

Data consistent with autoimmune disease being caused by Epstein-Barr virus are shown. Some of the features of the mechanism in the specific example of the anti-Sm autoantibody response were found in systemic lupus erythematosus. Based on this evidence, an effective vaccine would prevent the autoimmune disease in those vaccinated, modified or administered so that the vaccine is not itself capable of inducing autoimmune disease. In the case of anti-Sm, structures to be avoided in an Epstein-Barr virus-derived vaccine have been identified.

Differences have been identified in the immune responses to Epstein-Barr infection between individuals who develop a specific autoimmune disease and those who do not. These differences are used to distinguish those who are at greater risk for developing specific autoimmune diseases from those who are a lesser risk.

Assuming Epstein-Barr virus causes autoimmune disease and that Epstein-Barr virus remains latent in the patient for life, reactivation of the virus from the latent state is important in generating or maintaining the autoimmune response that culminates in autoimmune disease. Cells infected with latent virus may also encourage autoimmunity. Based on the understanding that reactivation or latency are important to produce or sustain autoimmunity, then therapies directed against Epstein-Barr virus will also be effective therapies for the autoimmune manifestations of disease for which Epstein-Barr virus is responsible.

BRIEF DESCRIPTION OF THE DRAWINGS

FIG. 1A shows the background reactivity of the octapeptides with anti-human IgG conjugate alone. FIG. 1B shows the reactivity of the octapeptides with a normal human serum. FIG. 1C shows binding of a serum from a patient with systemic lupus erythematosus who precipitates the nRNP autoantigen, but not Sm autoantigen. FIG. 1D demonstrates the reactivity of a representative patient who has both anti-Sm and anti-nRNP autoantibodies as determined by specific precipitin formation in Ouchterlony immunodiffusion. From J. A. James and J. B. Harley (*J. Immunol.* 148;2074-2079, 1992).

FIG. 4A presents an example of the background binding found from a normal human serum. FIG. 4B presents the binding of the first serum available after presentation with lupus (from April, 1986) and FIG. 4C and 4D present the binding of subsequent sera (from July, 1987 and December 1988, respectively). Solid arrows indicate the PPPGMRPP (SEQ ID NO:4) octapeptides and the open arrow the PPPGIRGP (SEQ ID NO:5) sequence. From J. A. James et al (*J. Exp. Med.* 181:453-461 (December 1995)).

FIGS. 5A-C are graphs of the binding of PPPGRPP-MAP™(SEQ ID NO:1)-immunized rabbit sera and a Freund's control serum to the PPPGRRP-MAP™ (FIG. 5A); SEQ ID NO:1, PPPGMRPP-MAP™ (FIG. 5B); SEQ ID NO:4, and nRNP/Sm antigen (FIG. 5C) by solid phase ELISAs (enzyme-linked immunosorbent assays). The bleeds of the rabbits are along the abscissa and the absorbance (X 1000) on the ordinate. The preimmune serum (pb) and post-immunization bleeds 1 through 14 (Im1 to Im14) which span 52 weeks are indicated. The PPPGRRP (SEQ ID NO:1) peptide is found in the Epstein-Barr virus Nuclear Antigen-1 (EBNA-1).

FIG. 8A is from a normal who has no evidence of having been infected by Epstein-Barr virus by the assay for anti-Epstein-Barr virus Viral Capsid Antigen IgG. The other sera presented (FIGS. 8B through 8E) are all positive in this assay.

DETAILED DESCRIPTION OF THE INVENTION

Figure 1A:
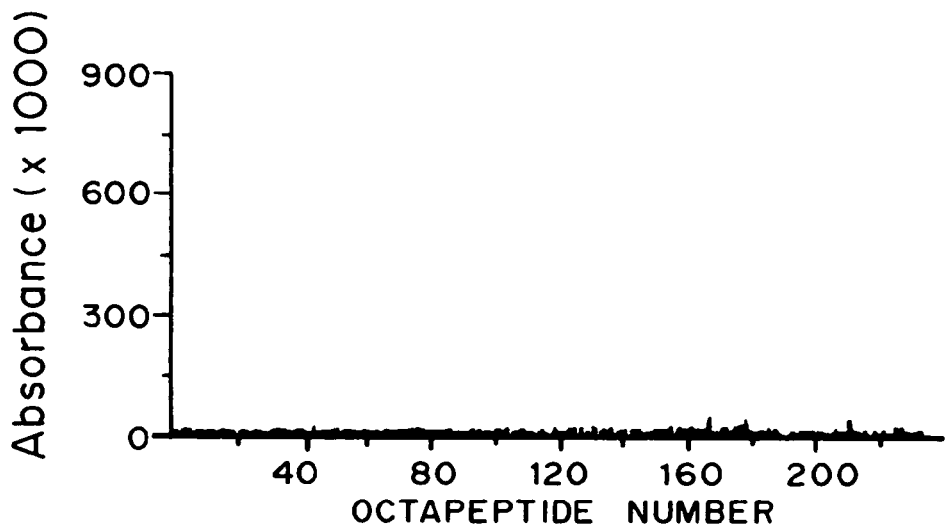
FIGS. 1A-D, graphs of absorbance indicative of the antigenicity of overlapping octapeptides of an Sm B/B' polypeptide. Each number along the abscissa indicates the first amino acid of an octapeptide that begins with this amino acid (octapeptide number, 1-8, 2-9, 3-10, etc.). Each octapeptide overlaps its neighbor by seven amino acids.
Figure 1B:
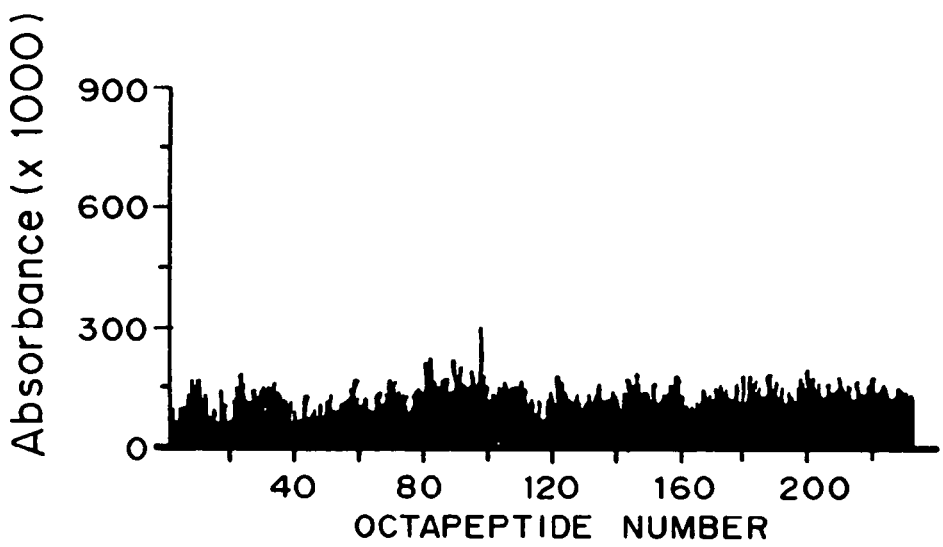
Figure 1C:
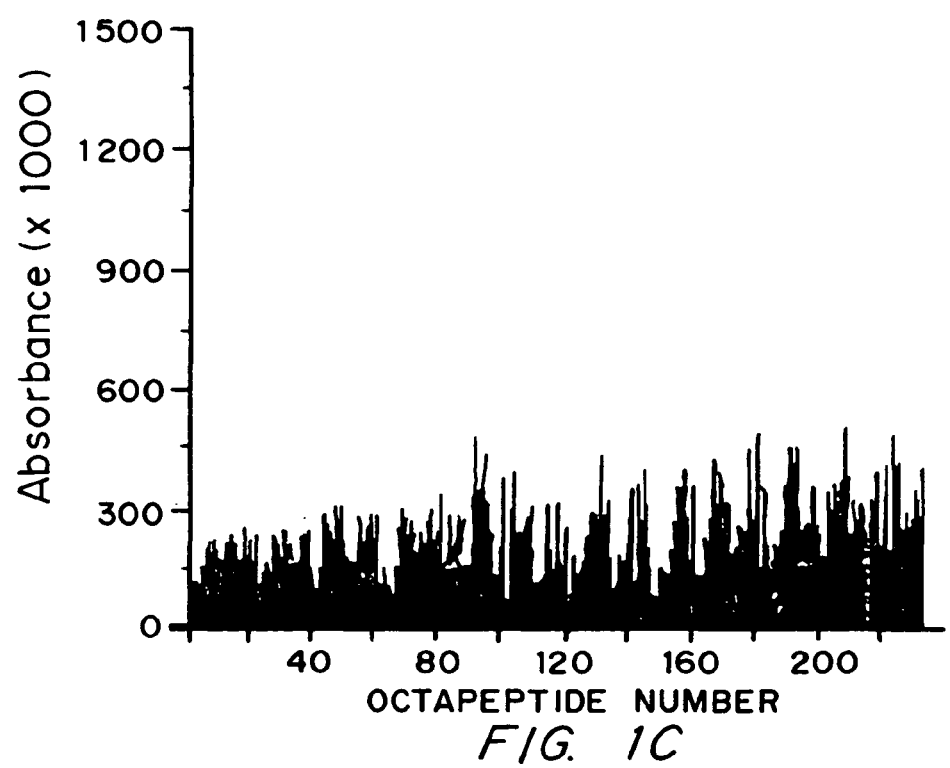

In the United States, about 95% of the adult population has been, and continues to be, infected with Epstein-Barr virus. Observations described herein are consistent with a small proportion of these developing autoimmune disease, related to this virus. Other factors are also likely to be important in the development of autoimmune disease, but are not essential to understand in order to develop therapeutics and diagnostics for use in diagnosing, treating and preventing or ameliorating autoimmune diseases involving Epstein-Barr virus as the etiologic agent. Epstein-Barr virus is the probable etiologic agent for nearly all cases of lupus, which serves as an example of autoimmune disease.

Diagnostics and therapeutics derived from the discovery that Epstein-Barr virus causes autoimmune disease as applied to the prevention, diagnosis and treatment of autoimmune disease are described herein. Systemic lupus erythematosus (lupus) is the particular autoimmune disease evaluated and for which data have been obtained. Within lupus, the work on a molecular understanding of the relationship between anti-Sm and systemic lupus erythematosus and the relationship of anti-Sm autoantibodies to Epstein-Barr virus is the best illustration of the data supporting these diagnostics and therapeutics.

The experiments described herein to address Epstein-Barr virus in lupus were guided by the results of immunochemical studies, not by the previous studies. These data pointed toward a curious mechanism in the anti-Sm autoantibody system in lupus which could involve Epstein-Barr virus.

The technology applied to the problem is very important in two ways. First, the assays for anti-Epstein-Barr virus antibodies have been dramatically improved. The classic method is to evaluate antibody binding to an Epstein-Barr virus infected cell line by immunofluorescence. This assay is dependent upon the expression of different Epstein-Barr virus proteins, depending upon whether the cell line is producing virus or the virus is latent. The autoantibodies of lupus often render these assays uninterpretable, making their use in lupus especially problematic.

Consequently, solid phase assays using enriched preparations of the surface antigen constitute a major improvement. The surface antigen is largely composed of a glycoprotein called gp340/220 or the Viral Capsid Antigen. These preparations of surface antigens have had many interfering substances removed. Epstein-Barr virus infection in man virtually always generates antibodies against this surface antigen. The assay is much simpler than is the cell line immunofluorescence assay and subject to much less variation in interpretation.

Second, molecular methods have been designed and developed to detect Epstein-Barr virus which appear to be at least as reliable as the serologic methods, and may even be superior. In normal adults Epstein-Barr virus infects only about one in every 20,000 to 500,000 B cells (Miyashita, E. M. et al. Cell 80:593-601 (1995)). B cells usually constitute only about 8% of the peripheral blood mononuclear cells. The vanishingly small quantity of Epstein-Barr DNA is lost in a relative ocean of genomic human DNA and is very difficult to detect. The improved sensitivity and specificity of detection of Epstein-Barr virus DNA improves the measurement made and leads to more accurate interpretation of the data. The older methods detected Epstein-Barr virus DNA in the peripheral blood in about 70% of individuals who had serologically converted, while the method described herein appears to detect more than 95% of those who have seroconverted and a few who have not seroconverted.

Reliable assays were used to address the prevalence of seroconversion and infection in the cases and controls in a way that took optimal advantage of the known properties of the viral infection. Others have selected sub-optimal study populations, have poorly chosen their controls, or have focused upon the quantitative level of antibody rather than qualitative evidence for infection, in addition to the technical problems outlined above in reliably detecting anti-Epstein-Barr virus seroconversion and Epstein-Barr viral DNA.

The data in the anti-Sm autoantibody system, discussed below, are used as a model in which the antigen presenting capacity of the B cell is important in generating autoimmunity. For example, the PPPGRRP (SEQ ID NO:1) structure is found in Epstein-Barr virus Nuclear Antigen-1. This sequence induced autoimmunity against the Sm B/B' of a rabbit after immunization. This autoimmunity not only included the related PPPGMRPP (SEQ ID NO:4) of Sm B/B', but also many other structures of B/B'. When the B cell generates a receptor that binds PPPGRRP (SEQ ID NO:1) and PPPGMRPP (SEQ ID NO:4) then this B cell is capable of presenting the spliceosome to the immune system. Of course, once this cross reacting autoantibody is produced, then it may facilitate spliceosomal autoimmunity. Epstein-Barr virus is important because the immune control of the infected B cell is altered by the infection, rendering autoimmunity more likely. This mechanism can be directly extended to other antigens to generate other immune responses (both cellular and humoral) which lead to a variety of autoimmune diseases. Also, double infection with Epstein-Barr virus and another virus would extend the immune regulatory abnormalities to the antigens of the second virus.

Autoimmune Diseases

There are a large number of disorders in man that are thought to be autoimmune. These include systemic lupus erythematosus, autoimmune thyroid disease (Graves' disease or Hashimoto's thyroiditis), autoimmune beta islet disease of the pancreas (more commonly referred to as juvenile or Type 1 diabetes mellitus), primary biliary cirrhosis and many others. The particular disorders listed above are thought to involve antibodies produced in the host (the patient, in this instance) which bind to constituents of self. These antibodies are called autoantibodies. The particular constituent of self bound by the autoantibodies is associated with the different disorders. For example, anti-mitochondrial autoantibodies are associated with primary biliary cirrhosis. Anti-acetylcholine receptor autoantibodies are associated with myasthenia gravis. The list of such autoantibodies is quite long and often only one or a few autoantigens are bound by autoantibodies in each particular disorder. Systemic lupus erythematosus (or abbreviated as lupus herein) is an exception to this tendency, since many autoantibodies may be found in the disease and since patients do not necessarily share any particular autoantibody specificity. Anti-Sm (which is an anti-spliceosomal autoantibody specificity) is one of the autoantibodies closely associated with systemic lupus erythematosus, but even this autoantibody is found in only a minor fraction of patients with systemic lupus erythematosus. (Please refer to a review of this area (Harley, J. B. and Gaither, K. K. *Rheum. Dis. Clin. N. Amer.* 14:43-56 (1992)).

It is not sufficient just to produce autoantibodies. There must be some consequence of their presence in order to develop pathology which culminates in clinical disease. There are many instances of detecting autoantibodies in the absence of any detectable clinical illness. Autoantibodies may realize their pathologic potential by binding their antigen in the circulation. They then become part of circulating immune complexes. They may deposit in tissues, induce an inflammatory response, and cause tissue injury, as appears to occur in lupus. Autoantibodies may interfere with the functioning of receptors or otherwise activate cells as may happen in Wegener's granulomatosis or Graves' ophthalmopathy. Autoantibodies may simply block normal functioning of a protein, as happens to the acetylcholine receptor in myasthenia gravis. No doubt there are other mechanisms by which autoantibodies encourage clinical illness.

These mechanisms involve humoral autoimmunity; that is, autoimmunity that is mediated by autoantibodies. There is another form of autoimmunity mediated by cells, in particular T cells. Multiple sclerosis is thought by some to be an example of a disease that is mediated by autoimmune T cells. Although the methods and compositions described herein are particularly concerned with humoral autoimmunity, it is expected that cellular autoimmune processes are also involved with producing autoimmunity as a consequence of Epstein-Barr virus infection. As in many situations, one skilled in the art would expect cellular immune mechanisms to dominate in some individuals and humoral mechanisms to dominate in others. This situation would be expected to give rise to different clinical expression of disease. Tuberculous and lepromatous leprosy are examples where differences in the dominant form of the immune response lead to profound differences in the clinical illness, despite being caused by the same organism.

The traditional distinction between humoral and cellular immune mechanisms are being reevaluated under a new paradigm. T cells appear to have the capacity to respond in at least two ways. These cells are called Th1 and Th2, for T helper cells, Type 1 and 2. Characteristic cytokine production profiles are often used to distinguish these different responses. Th1 responses tend to be the more traditionally appreciated cellular immune responses. Th2 responses lead, among other consequences, to more of an antibody response and are more aligned with the classic humoral response. However, these boundaries do not appear to operate strictly since some types of antibody are more likely found in Th1 responses and the Th2 response clearly has its cellular component. Most autoimmune diseases probably have important components of both humoral and cellular autoimmunity.

Below, systemic lupus erythematosus is used as a particular example of an autoimmune disease. Data are presented which is consistent with the position that Epstein-Barr virus causes this autoimmune disorder. Lupus is one of many autoimmune diseases that are likely to share basic features, such as the causative agent being Epstein-Barr virus.

Definitions:

As used herein, autoimmune diseases are diseases that are primarily autoimmune, as well as diseases which do not appear to be primarily autoimmune but have immune manifestations involving immunoglobulins, antigen specific B cell surface receptors (surface immunoglobulin), or antigen-specific T cell receptors. Examples of diseases which fall into these categories are systemic lupus erythematosus, Sjogren's syndrome, rheumatoid arthritis, juvenile onset diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, primary biliary cirrhosis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, autoimmune hemolytic anemia, pemphigus vulgaris, pemphigus, bullous pemphigoid, dermatitis herpetiformis, alopecia areata, autoimmune cystitis, pemphigoid, scleroderma, progressive systemic sclerosis, CREST syndrome (calcinosis, Raynaud's esophageal dysmotility, sclerodactyly, and telangiectasia), adult onset diabetes mellitus (Type II diabetes), male or female autoimmune infertility, ankylosing spondylitis, ulcerative colitis, Crohn's disease, mixed connective tissue disease, polyarteritis nodosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, postcardotomy syndrome, Cushing's syndrome, autoimmune chronic active hepatitis, bird-fancier's lung, asthma, allergic disease, allergic encephalomyelitis, toxic necrodermal lysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, chronic fatigue syndrome, fibromyalgia, Takayasu's arteritis, Kawasaki's disease, polymyalgia rheumatica, temporal arteritis, schistosomiasis, giant cell arteritis, ascariasis, aspergillosis, Sampter's syndrome (triaditis also called, nasal polyps, eosinophilia, and asthma), Behcet's disease, Caplan's syndrome, dengue, encephalomyositis, endocarditis, myocarditis, endomyocardial fibrosis, endophthalmitis, erythema elevatum et diutinum, psoriasis, erythroblastosis fetalis, fascitis with eosinophilia, Shulman's syndrome, Felty's syndrome, filariasis, cyclitis, chronic cyclitis, heterochromic cyclitis, Fuch's cyclitis, IgA nephropathy, Henoch-Schonlein purpura, glomerulonephritis, graft versus host disease, transplantation rejection, cardiomyopathy, Alzheimer's disease, parvovirus infection, rubella virus infection, post vaccination syndromes, congenital rubella infection, Hodgkin's and non-Hodgkin's lymphoma, renal cell carcinoma, multiple myeloma, Eaton-Lambert syndrome, relapsing polychondritis, malignant melanoma, cryoglobulinemia, hepatitis B virus infection, hepatitis C virus infection, Waldenstrom's macroglobulinemia, mumps virus infection, and any other disorder in which the specific recognition of the host by immunoglobulin, B cell surface receptor (surface immunoglobulin), or T cell receptor is suspected or shown to be important in any aspect of the pathogenesis of the clinical illness.

Immunization is any procedure which leads to a cellular or humoral immune response directed against an identifiable and specific antigen, usually the immunogen. An antigen is a substance that is bound by antibody. Sometimes an antigen is also referred to when meaning a substance against which any immune response is directed and that it may be bound by antibody or lead to a cellular immune response. An autoantigen means a constituent of self that binds antibody (making it an autoantibody) or that induces a cellular response, for example, by a T cell. The spliceosome is that molecular apparatus, composed of RNA and protein, which splices heteronuclear RNA, thereby removing the introns from the coding sequence of RNA. The cellular response may be assayed by presentation of a peptide from the autoantigen, proliferation, cell activation, the prevention of cell activation, secretion of cytokines, activation of apoptosis, or other indication of an effect of the presence of the autoantigen. An autoantibody is any immunoglobulin, antigen specific B cell surface receptor (surface immunoglobulin), or antigen specific T cell receptor directed against self protein. Such T cell receptors usually bind peptides which themselves are bound by histocompatability molecules. The T cell receptor usually binds to both the peptide and the histocompatibility molecule.

Therapy is a treatment by medical or physical means. A "treatment" is the composition used for treating a condition. Antiviral therapy is the use of a treatment in an effort to suppress or eliminate a virus, for example, suppression, elimination or other ameloiration of the effect of Epstein-Barr virus. Peptides are small proteins composed of amino acids covalently bound to one another by peptide bonds. Peptides may be prepared by an in vivo mechanism, as in life, by using the nucleic acid encoding for the sequence of the peptide produced, or in vitro using peptide chemistry. A vaccine is a composition or preparation that is used in an attempt to prevent a disease or ameliorate a disease. A disease is any illness.

Seroconversion means that the subject has developed antibodies of sufficient magnitude in the serum to conclude that the subject has made an immune response against the agent or substance of interest. Usually, this is the result of immunization (vaccination) or infection. Seropositive means that there are a sufficient quantity of antibodies with sufficient affinity to conclude that seroconversion has occurred. Seronegative means that the quantity and affinity of antibodies are not sufficient to conclude that seroconversion has occurred. In this application, the terms "lupus" and "systemic lupus erythematosus" are used interchangeably.

The single amino acid code is used in the figures and following examples, as follows:

| | | |
|---|---|---|
| A - alanine | I - isoleucine | R - arginine |
| C - cysteine | K - lysine | S - serine |
| D - aspartic acid | L - leucine | T - threonine |
| E - glutamic acid | M - methionine | V - valine |
| G - glycine | P - proline | Y - tyrosine |
| H - histidine | Q - glutamine | |

Therapeutic and Diagnostic Compositions Vaccines

Immunity against a viral infection can be induced using either peptides, viral proteins or other components of the virus such as carbohydrate components, substances which imitate structures of the virus, or the virus. In the preferred embodiment, the vaccine is based on the viral proteins wherein the epitopes cross-reactive with the splicesomal proteins are deleted. In other embodiments, the vaccine is based on viral proteins where epitopes cross-reactive with antibodies to other known autoantigens are deleted or altered to decrease their immunoreactivity with autoantibodies. In still other embodiments, the vaccine includes the virus, either live, modified or inactivated, or components thereof, in a vehicle which can be administered in a dosage form and over a schedule eliciting a strong immune response to kill the virus, but which does not elicit an autoimmune response.

An unmodified vaccine may be useful in the prevention and treatment of autoimmune disease related to Epstein-Barr virus. The dose, schedule of doses and route of administration may be varied, whether oral, nasal, vaginal, rectal, extraocular, intramuscular, intracutaneous, subcutaneou, or intravenous, to avoid autoimmunity and, yet, to achieve immunity from Epstein-Barr virus infection. The response to the unmodified vaccine may be further influenced by its composition. The particular adjuvant employed (its concentration, dose and physical state), concentration of the virus in the vaccine, and treatment of the unmodified vaccine with physical environmental changes, for example, temperature and pressure, the particular buffer, and the particular preservative(s) (if any) will be selected to reduce the liklihood of developing an autoimmune disorder, for example using the animal strains discussed below. This same or different vaccine may be useful in reducing or eliminating the effect of an existing latent or active Epstein-Barr virus infection upon autoimmunity.

Peptides of up to about forty amino acids, more preferably between four and twenty-five amino acids, most preferably eight amino acids, can be synthesized using any one of the methods known to those skilled in the art. In general, an epitope of a protein is composed of between three or four and eight amino acids (see Watson et al., "Certain Properties Make Substances Antigenic," in *Molecular Biology of the Gene,* Fourth Edition, page 836, paragraph 3, (The Benjamin/Cummings Publishing Company, Menlo Park, 1987). As used herein, the peptides can contain the entire native epitope, or portions thereof sufficient to react with autoantibody.

Although described in the literature with reference to specific sequences encoding viral proteins or the autoantigens, a number of substitutions using natural or synthetic amino acids can be made in the peptides to yield an peptide acting as a linear epitope that is functionally equivalent to the disclosed sequences, for example, as demonstrated by James and Harley, *J. Immunology* 148:2074-2079 (April 1992). Accordingly, the term linear epitope as defined by a specific sequence is used herein to include peptides having substitutions yielding a peptide bound in an equivalent manner or extent by an antibody or autoantibody. For example, using monoclonal antibodies against peptide determinants of Sm B/B', substitution studies demonstrated that A, G, and S can substitute for R in PPPGMRPP (SEQ ID NO:4) in the binding of one antibody, KSm3. Analogously, F, H, T, V and Y can substitute for I in PPPGIRGP (SEQ ID NO:5) in the binding of KSm3.

Solid phase binding of autoantibodies to peptides has proven useful for examining sequential linear epitopes, also referred to as "linear" or "sequential". These have been useful to define important residues in epitope structure. This approach may or may not be less useful in defining conformational epitopes or regions where two or more linear, but not sequential, epitopes are brought together by the tertiary structure. The particular structural relationships between the autoantigens and autoantibody with particular regard to the particular conformation assumed by the peptide determines what can be learned by this approach. In addition, although many peptides may assume conformations in solution that are not found in the native protein structure, true epitopes may still be delineated by this method. Those peptides that tend to have a structure similar to that found in the native molecule are expected to usually be bound by a larger proportion of the autoantibodies that bind the analogous sequence on the native protein and/or may be bound with greater affinity.

It is believed that naturally arising human lupus follows a progression similar to that induced in the rabbit model described in the examples. Using this model, an immune response to a peptide, one very similar to a region of EBNA-1, is the seminal, initiating event for the subsequent autoimmunity and disease manifestations of lupus, where they occur. A structure, such as a peptide, that is capable of inducing autoimmunity is not necessarily identical to the structure found in the autoantigen. Indeed, it is possible that these structures would commonly be at least slightly different, when comparing the substance that induces the autoimmune response and the analogous structure in the autoantigen. On the other hand, there must be a basis for the non-autoantigen substance to induce autoimmunity. This is best identified as a cross-reaction wherein the immune recognition molecule binds, though not necessarily equally, to both the non-autoantigen substance as well as to the autoantigen.

The proposed mechanism is as follows. An immune response against a non-autoantigenic substance occurs. Some fraction of the antibodies thereby produced recognize the autoantigen and hence are autoantibodies. These autoantibodies facilitate the processing and antigen presentation of the autoantigen via the B cell surface immunoglobulin which serve as receptors, in this case for autoantigen, or via immunoglobulin cell surface receptors that are found on a variety of cells capable of antigen presentation. Once this occurs the immune response expands to other structures of the autoantigen and a full-blown, complete autoimmune response against the autoantigen ensues, which can result in clinical illness.

Based on this mechanism, the autoimmune responses progress from one or a few initial antigenic structure(s) to a much more complex response focused upon the autoantigen. Elucidating the pattern of progression and understanding the relationship of autoimmune serologic findings to clinical manifestations places the physician in a strong position to accurately prognosticate and prepare patients and their families for the more likely outcomes.

In the case of systemic lupus erythematosus and the anti-Sm response, one method is to repeat the assays determining autoantibody binding to peptides over time. The effect of the peptide in vitro on cells from patients can also be measured. Proliferation, secretion of cytokines, interferons and other substances, expression of cell surface molecules and activation are typically useful diagnostic indicators.

This strategy to generate autoimmunity can also be used to develop reagents that are useful in diagnosis or treatment of autoimmune disorders. Animal antibodies that compete with or otherwise facilitate the identification of particular fine specificities of binding can be important in evaluating prognosis. Moreover, the peptide binding pattern to the octapeptides from the nRNP A protein show two different patterns. It should be possible to correlate a particular pattern found in a patient to obtain an indication of the stage the disease currently is at as well as the clinical prognosis. Reagents developed as a consequence of immunizing animals with autoantigenic peptides could be used to identify these differences. Such reagents include antisera, T cell lines, subsets of antibodies, individual antibodies, subsets of cells bearing a subset of the T cell receptors, individual T cell receptors, and cytokines and other substances elaborated by cells from the animal. The antibodies and T cell receptors are construed to include recombinant antibodies or T cell receptors derived from a peptide-immunized animal.

The RNA-protein particles which are the major autoantigens may now be purchased commercially. The reagents made available by the animal model of autoimmunity described herein will be useful in the manufacturing and testing of autoantigens. Affinity purification using animal antiserum (absorbed or otherwise prepared) could be used for purification of the naturally occurring autoantigens.

Having a mechanism of disease provides the opportunity to apply new strategies for prevention of disease and for specific immunologic correction of the immune abnormalities that lead to disease, and therefore more accurately design the therapy.

For example, with the realization that the generation of autoimmune disease can be divided into phases comes the appreciation that the therapeutic opportunities will be similarly partitioned. As a specific example, the influence of vaccination with an analog of PPPGMRPP (SEQ ID NO:4) will be different depending not only upon the structure of the immunogen, but also upon the pharmaceutical carrier, upon the maturity of the autoimmune response against PPPGMRPP (SEQ ID NO:4) and Sm, and upon other therapeutics that may be administered concomitantly. Such therapeutics include drugs as well as biologics, such as cytokines, immunoglobulins, and interferons, among others.

As a second specific example, mice strains exist which produce lupus autoimmunity, as well as strains which do not produce lupus autoimmunity, after immunization with PPPGMRPP-MAP™ (SEQ ID NO:4). The genetic, biochemical, and physiological differences between these strains can be used to develop diagnostics, including gentic markers and risk factors, and therapeutics for autoimmune disease, especially lupus, using techniques known to those skilled in the art.

As discussed above, based on the data confirming that Epstein-Barr virus is an inducing agent for lupus, it is possible to design therapeutics to prevent or inhibit further progression of lupus by vaccinating with Epstein-Barr virus, or components thereof, using standard vaccination procedures, most preferably after alteration or removal or masking of the sites which elicit the autoimmunity.

The peptides can be used therapeutically in combination with a pharmaceutically acceptable carrier. The peptides can be administered in a dosage effective to block autoantibodies or as a vaccine to block the production of autoantibodies, by eliciting a protective immune response against non-autoantigenic regions of the pathogen. The peptide acts as a functional antagonist by binding to antibody that does not stimulate or activate the immune cells and thereby block the immune response to the autoantigens.

Pharmaceutical carriers are known to those skilled in the art. These most typically would be standard carriers for administration of vaccines to humans, including solutions such as sterile water, saline, and buffered solutions at physiological pH. Peptides used as vaccines are most preferably administered intramuscularly or subcutaneously. Other compounds will be administered according to standard procedures used by those skilled in the art.

Alternatively, the peptides used for treatment might include peptides homologous to an identified antigenic sequence. These peptides, either free or bound to a carrier, could be delivered to a patient in order to decrease the amount of circulating antibody with a particular specificity. In addition, knowledge of the cross-reacting epitopes between a foreign antigen and an autoantigen may allow for re-induction of tolerance. It is well known in experimental models of the immune response that the response can be suppressed and tolerance induced by treatment with the antigen. Peptide therapy with the cross-reacting sequences may be a useful therapy in autoimmune diseases.

The amino acid sequences can also be used to make agents for neutralizing circulating antibodies or immobilized on substrates in extracorporeal devices for specific removal of autoantibodies, using methodology known to those skilled in the art.

Diagnostics

Individuals who are not at as great a risk for developing autoimmune disease can be identified by reactivity to the various peptides, for example, as demonstrated in the examples where individuals who are not prone to develop lupus are characterized by antibodies to GAGAGAGAGAGAGAGAGAGAGAGA (SEQ ID NO:7). Other structures derived from Epstein-Barr virus can be used to predict who will develop autoimmune disease. For example, GAGAGAGAGAGAGAGAGAGAGAGA (SEQ ID NO:7) is a commonly identified antigen from Eptein-Barr virus in normal individuals, while lupus patients do not tend to bind this structure. An individual identified at risk for the development of an autoimmune disease, but who does not yet manifest autoimmunity or symptoms of the disease, may require a special therapeutic approach. This is an opportunity to induce immune suppression before the process leading to autoimmune disease is initiated. Strategies such as intravenous administration of large amount of the initiating structure is known to induce tolerance. Small sub-immunogenic doses of the initial immunogen can also be used to induce tolerance.

There is a limited opportunity to interrupt or redirect an immune response that has been initiated against the first components of the autoantigen. Here again the induction of suppression by the use of the component peptides or analogs thereof with or without concomitant drugs or biologics has the potential to inhibit progression into an autoimmune disorder. Once autoimmunity against the autoantigen is established, the use of component peptides or their analogs with or without concomitant drugs or biologics may interrupt the course of the autoimmune response, thereby ameliorating the illness.

The animal model provides an opportunity to optimize ways of interrupting and reversing the autoimmune process. For example, it has been observe that one of the rabbits immunized with Map-PPPGMRPP (SEQ ID NO:4) seemed to improve clinically somewhat after developing the most severe manifestations of systemic autoimmunity. If this result is the effect of a particular antibody, then this antibody may have the capacity to influence the maturation of the immune response toward alleviating the disease in other species. For example, such an antibody could be isolated by biochemical methods, by recombinant DNA methods or by hybridoma monoclonal methods, humanized using standard technology and then administered to patients as a specific therapeutic agent for disease. T cell receptors or cytokines could be equally useful.

Assays

Subsets of antigenic peptides have the potential to identify patients at risk for particular clinical manifestations or patients in particular prognostic groups. The peptides can be used in combination in assays, such as the solid phase assay, to classify patients.

Specifically, the peptides that are bound by autoantibodies in patients characterized by specific disorders, such as renal disease or central nervous system involvement, are selected and combined in an assay, such as an ELISA for a test to detect the collection autoantibodies that bind this particular collection of peptides. Using a mixture of peptides may increase the efficiency and reliability of such assays, as compared with using a single autoantigen, or a single peptide.

The peptides can be used in solution or immobilized to a solid substrate, such as a gel suitable for affinity chromatography, or a multi-well plate, using standard techniques such as the commercially available cyanogen bromide.

The present invention will be further understood by reference to the following non-limiting examples.

EXAMPLE 1

The relationship of anti-Sm to Epstein-Barr virus.

The anti-Sm and anti-nuclear ribonucleoprotein (nRNP) autoantibody specificities have an Ouchterlony precipitin reaction of partial identity. This is because the epitopes bound are found on two antigens which share some, but not all antigenic features. The Sm autoantigen may be found in association with the U1, U2, U5 or U4/6 spliceosomal particles. These are composed of specific U RNA and particular peptides. The nRNP autoantigen is composed of only U1 RNA and particular unique peptides. The anti-Sm antibodies bind to the B/B' or D spliceosomal peptides in Western blot while the anti-nRNP autoantibodies bind 70K, A or C peptides (Lerner, M. R. and Steitz, J. A. *Proc. Natl. Acad. Sci. USA* 76:5495-5499 (1979); Hinterberger, M. *J. Biol. Chem.* 258: 2604-2613 (1983); and Petterson, I. et al. *J. Biol. Chem.* 259:5907-5914 (1984)). (B/B' and D are found in the U1, U2, U5 and U4/6 spliceosomal particles. A protein termed the N protein or the Sm N protein is closely related to B and B'. 70K, A and C are usually only found in U1.) Anti-Sm precipitins are found in about 10% to 20% of lupus patients. Anti-Sm is sufficiently specific for this diagnosis that its presence in the serum has become part of the 1982 Criteria for the Classification of Systemic Lupus Erythematosus (Tan E. M., et al *Arthritis Rheum.* 25:1271-1277 (1982)).

Antigenicity of B/B' peptides assessed by measuring antibodies binding to octapeptides synthesized in vitro from the sequence of the B/B' Sm peptide.

Figure 1D:
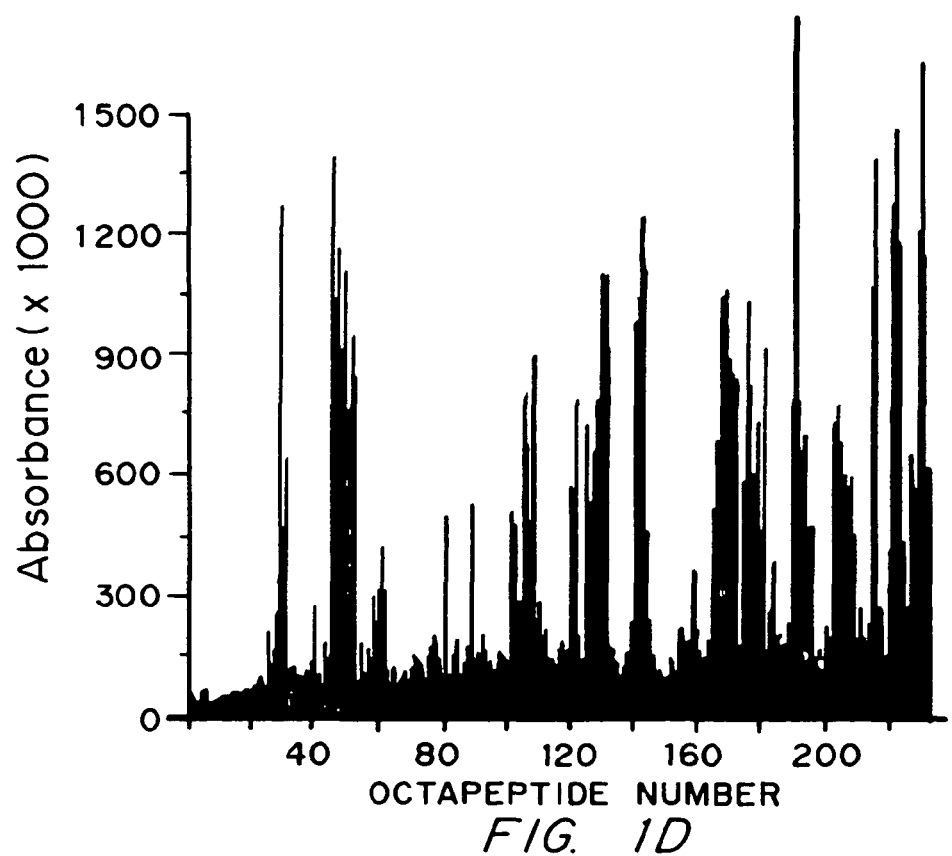
Figure 2:
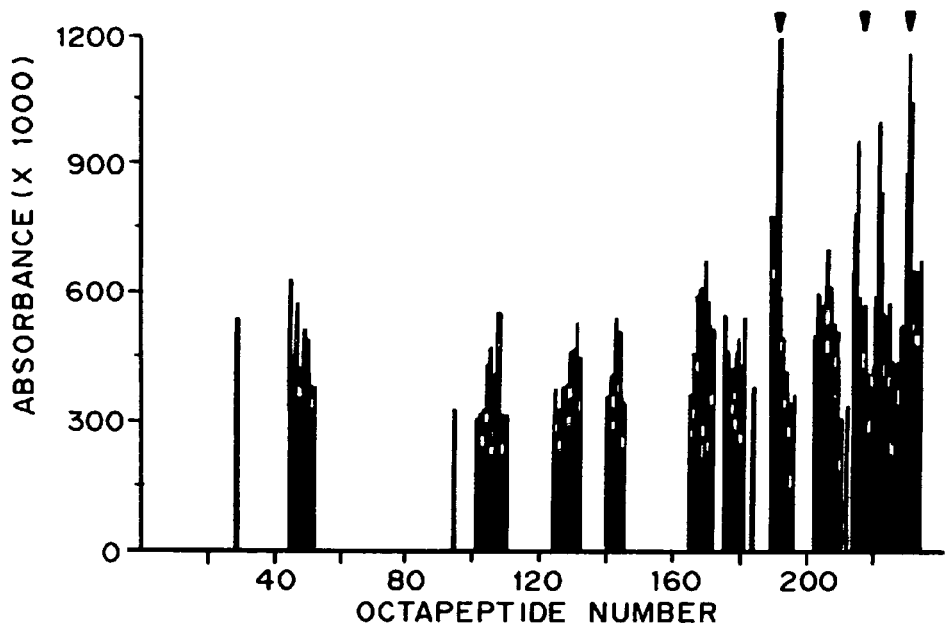
FIG. 2. Mean binding to overlapping octapeptides by Sm and nRNP precipitin positive lupus patients showing the major epitopes (as defined as being greater than 0.5 O.D., or a mean of 10 standard deviations above the mean binding of normal sera). Binding below the threshold of 0.325 O.D., or the mean of normals plus two standard deviations, has been omitted for clarity. The standard error is depicted as an open box below the mean in the bar representing the mean of the lupus patient binding. From J. A. James and J. B. Harley (*J. Immunol.* 148;2074-2079, 1992).

The autoantigenicity of Ro (also known as the SS-A) autoantigen was reported by Scofield, R. H. et al. *Proc. Natl. Acad. Sci. USA* 81:3343-3347 (1991). The antigenicity of the B/B' peptides was assessed by measuring antibodies binding to octapeptides synthesized in vitro from the sequence of the B/B' Sm peptide, as described by James, J. A. and Harley, J. B. *J. Immunol.* 148:2074-2079 (1992). Representative data from an anti-Sm precipitin positive patient are shown in FIG. 1D and controls in Figures A-C. Note that eleven groups of peptides are bound by the sera containing anti-Sm autoantibody. One of the most unexpected observation was that all of the anti-Sm sera tested bound almost the identical octapeptide structures (FIG. 2).

The sequence PPPGMRPP (SEQ ID NO:4) is repeated three times in Sm B' (Van Dam, A. et al. *EMBO J.* 8:3853-60 (1989)). The N protein, which is very homologous to the B/B' protein, has three repeats of PPPGMRPP (SEQ ID NO:4) and a closely related sequence PPPGIRGP (SEQ ID NO:5) is also found once (Schmauss C. et al. *Nuc. Acid Res.* 17:1733-43 (1989)). PPPGIRGP (SEQ ID NO:5) is not found in the B' protein; rather, PPPGMRGP (SEQ ID NO:8) is found in its place. Much confusion has surrounded this area due to the original publication of the Sm B/B' sequence (Rokeach L. A. et al. *J. Biol. Chem.* 264:5024-30 (1989); Sharpe N. G. et al. *FEBS Lett.* 250:585-90 (1989)) which was later found to actually produce what is now termed the N protein or the Sm N protein (Schmauss C. et al. *Nuc. Acid Res.* 17:1733-43 (1989)). Lupus patients with anti-Sm precipitins all have antibodies which bind to both Sm B (a truncated version of Sm B'), Sm B' and Sm N. Substantial cross-reactivity occurs between the three proteins.

Such repeated structures are sometimes particularly immunogenic. These anti-Sm sera also bind to some of the known sequences which are structurally similar to PPPGMRPP (FIG. 3; SEQ ID NO:4). These sequences included PPPGRRP (SEQ ID NO:1); which is found the Epstein-Barr Nuclear Antigen-1 (EBNA-1) protein. GRGRGRGG (SEQ ID NO:2) and RGRGREK (SEQ ID NO:3) are also sequences from Epstein-Barr virus Nuclear Antigen-1, but these are similar to a major antigenic epitope of Sm D in lupus patients, GRGRGRGRGRGRGRGRGRGRGGPRR SEQ ID NO:9; (James, J. A., et al. *Clin. Exp. Imunol.* 98:41-426 (1994)). (See GenBank accession code: gb-vi.ebv for sequences of Epstein-Barr virus proteins.) All three peptides appear to bind at least three times more antibody from the anti-Sm precipitin positive lupus patient sera than the controls. The antibody binding to these peptides in the lupus patient sera was over half of the antibody binding level found for PPPGMRPP (SEQ ID NO:4).

Serum samples from lupus patients stored early in the course of the disease process bind only PPPGMRPP (SEQ ID NO:4) and neighboring peptides) of the 233 possible octapeptides if B/B'

The analysis of stored sera revealed that a serum sample from an lupus patient stored early in the course of her disease process bound only PPPGMRPP (SEQ ID NO:4) (and neighboring peptides) of the 233 possible octapeptides of B/B' (FIG. 4) (James, J. A. et al. *J. Exp. Med.* 181:453-461 (December 1995)). This repeated PPPGMRPP (SEQ ID NO:4) motif is an early target in three additional patients tested from whom sera were available from early in their disease. In all of these patients PPPGMRPP (SEQ ID NO:4) is the first autoimmune epitope of the Sm B/B' autoantigen against which one can detect antibody binding. One interpretation of this finding is that PPPGMRPP (SEQ ID NO:4) is the first structure bound in at least some of those lupus patients who have anti-Sm autoantibodies. Most, if not nearly all, sera with anti-Sm have more complex binding when they present to their doctors with the illness. At this point no anti-Sm precipitin positive lupus patient who does not have antibodies to PPPGMRPP (SEQ ID NO:4) is known.

Antibodies directed against PPPGMRPP (SEQ ID NO:4) are a significant portion of the anti-Sm response in some patient sera. Five patient sera have been absorbed over columns composed of PPPGMRPP (SEQ ID NO:4). Four of these sera had anti-Sm and anti-nRNP precipitins and one had an anti-nRNP precipitin without anti-Sm; all five had anti-Ro autoantibodies which were above the normal range. The PPPGMRPP (SEQ ID NO:4) absorption removed 13 to 39% of the patient anti-Sm/nRNP response. These same column absorptions removed less than 10% of the anti Ro reactivity and over 95% of the anti-PPPGMRPP (SEQ IN NO:4) response. The proportion of the anti-Sm/nNRP activity absorbed varies with the number of the other octapeptides from Sm B/B' and D proteins bound by immune serum being tested.)

Rabbits immunized with PPPGMRPP (SEQ ID NO:4) developed antibody beyond the peptide of immunization which bound to many other octapeptides in the spliceosome, antinuclear autoantibodies, anti-double stranded DNA autoantibodies and clinical features that suggests the illness known in man as systemic lupus erythematosus Rabbits were immunized with PPPGMRPP (SEQ ID NO:4) on a MAP™ backbone (referred to as PPPGMRPP-MAP™ (SEQ ID NO:4) where the trademark refers only to the MAP™). These animals developed antibody beyond the peptide of immunization which bound to many other octapeptides in the spliceosome. These rabbits usually developed anti-PPPGMRPP (SEQ ID NO:4) antibodies along with anti-Sm and anti-nRNP autoantibodies, antinuclear autoantibodies, anti-double stranded DNA autoantibodies and clinical features that suggests the illness known in man as systemic lupus erythematosus. These rabbits variably had seizures, thrombocytopenia, proteinuria, renal insufficiency, cellular casts in the urine, hypoalbuminemia and alopecia (James, J. A. et al. *J. Exp. Med.* 181:453-461 (1995)). This has led to a new model of autoimmunity and suggests that a vigorous immune response against this one sequence, PPPGMRPP (SEQ ID NO:4), is sufficient to induce a specific autoimmune disease in some strains of animals.

PPPGRRP (SEQ ID NO:1) from the Epstein-Barr virus Nuclear Antigen-1 was found when the sequence was searched for sequences similar to PPPGMRPP (SEQ ID NO:4). To preliminary test whether it was possible for this sequence to induce spliceosomal autoimmunity, two rabbits were immunized with PPPGRRP-MAP™ (SEQ ID NO:4) following the protocol previously used with PPPGMRPP™ (SEQ ID NO:4). One of the two rabbits developed not only anti-PPPGMRPP (SEQ ID NO:4) antibodies, but also anti-spliceosomal autoantibodies and had B cell epitope spreading to regions of B/B' and D, as evidenced by antibody binding to other octapeptides (FIGS. 5 and 6).

If a structure from a virus could induce anti-spliceosomal autoantibodies when immunized in an animal then, this is evidence that this structure and the virus is important in the induction of the autoimmune disease associated with anti-spliceosomal autoantibodies, systemic lupus erythematosus.

These data suggest a sequence of events, as follows: infection with Epstein-Barr virus, development of anti-PPPGRRP (SEQ ID NO:1) antibodies, development of surface immunoglobulin (and secreted antibody) binding both PPPGRRP (SEQ ID NO:1) and PPPGMRPP (SEQ ID NO:4) (the first evidence of autoimmunity), antigen processing of the spliceosome bound by surface immunoglobulin (or soluble antibody) and presentation of the spliceosomal peptides, B cell epitope spreading (and perhaps T cell epitope spreading) and clinical features of lupus. Epstein-Barr virus infected cells are believed to encourage this sequence of events at a number of steps. By substituting another antigen for PPPGRRP (SEQ ID NO:1) and another autoantigen for PPPGMRPP (SEQ ID NO:4), this mechanism may generate lupus or another autoimmune disorder by following the same general sequence of events.

Genetic Linkages in Mice to Development of Lupus-like Autoimmunity After Immunization with PPPGMRPP-MAP™ (SEQ ID NO:4)

Experiments in mice have shown that there are some strains which develop lupus-like autoimmunity after immunization with PPPGMRPP-MAP™ (SEQ ID NO:4) and some that do not (J. A. James et al. *Arthritis Rheum.* 38:S226 (1995)). The difference between one responder (develops lupus-like autoimmunity) and one nonresponder mouse strain has been preliminarily localized to a region on mouse chromosome 4 (James, J. A. and Harley, J. B. *Arthritis Rheum.* 39:S216 (1996)).

This preliminary finding of linkage in this murine model of lupus suggest that the difference between the two parent strains of a recombinant inbred set of mice which determines the observable B cell epitope spreading and autoimmunity may be found at a single gene locus. This region of murine chromosome 4 does not contain immunoglobulin genes, T cell receptor genes, nor the histocompatibility genes which are highly variable polymorphic genes which determine so many other features of the immune response. The gene for CD72 is found here which may be important. Once the gene responsible for the observed effect is identified, then one skilled in the art can provide compositions for diagnosis, prevention and treatment of autoimmune disease. Beyond this specific example, it is expected that other genes and gene products will be shown to be important and analogous compositions will be obvious to one skilled in the art.

The host experiences changes after Epstein-Barr virus infection beyond the generation of an immune response. Gene expression and molecular machinery in infected cells is altered by the virus. These changes can be detected by those skilled in the art and used as diagnostics, as well as in the screening and development of therapeutics which are particularly important for individuals affected with or at risk of becoming affected with autoimmune disease.

EXAMPLE 2

Association of seroconversion against Epstein-Barr virus and an autoimmune disease.

Sera from lupus patients compared with controls were first tested for seroconversion against Epstein-Barr virus. There were a number of important considerations in designing these experiments. First, the older and more traditional assays for Epstein-Barr seroconversion were insufficiently specific. These assays are especially unreliable when applied to sera from lupus patients. Antinuclear autoantibodies in lupus sera often interfere with the test for Epstein-Barr seroconversion when an Epstein-Barr virus-infected cell line is used for the test. Both a positive test result for Epstein-Barr virus and for antinuclear antibodies involving the nuclear fluorescence of the cell line. Also, the infected cell line test for Epstein-Barr virus is often not positive in people known to have been infected with Epstein-Barr virus. Others have used such assays in patients with systemic lupus erythematosus with disappointing results (Tsai, Y. et al. *Int. Arch. Allergy Immunol.* 106:235-240 (1995)).

Second, in the United States as many as 95% of normal adults are infected with and have evidence of seroconversion against Epstein-Barr virus (Evans, A. S. and Niederman, J. C.: Epstein-Barr virus. In Viral Infections in Humans, 3rd ed. Evans, A. S. ed. pp 265-292 (Plenum, New York City 1989)). To detect a difference in adults above the 95% expected baseline of Epstein-Barr virus infection with confidence would require an unreasonably large number of patients and controls. On the other hand, in the United States, most people contract Epstein-Barr virus before the age of 20 years. Epstein-Barr virus causes infectious mononucleosis, also known as the "kissing disease", in some people. Controls who are children and adolescents will have a lower rate of infection than individuals who are older. By using younger patients and controls, it was thought that one might be able to collect a group of controls where the rate of Epstein-Barr virus seroconversion is less, perhaps less than 75%, thereby a sufficient increase in statistical power to enable this question to be addressed with the resources available.

The use of children and adolescents has nothing to do with anything unique or different about lupus in childhood or adolescence compared with the disease in adults. Rather, the younger cases represent the population in which the hypothesis of a relationship between Epstein-Barr virus infection and autoimmune disease can be most efficiently tested.

The most reliable test for seroconversion is against the Viral Capsid Antigen of Epstein-Barr virus, also called gp340/220 (and abbreviated as EBV-VCA). Solid phase assays are available for antibodies against this surface protein. The purification methods may include other proteins and antigens from Epstein-Barr virus, but as long as a substantial proportion of the preparation is composed of this surface antigen of Epstein-Barr virus, then the assay should be sensitive for an immune response directed against Epstein-Barr virus. The procedure used to isolate the antigen used in the commercial ELISA (enzyme-linked immunosorbent assay) kits has been described in detail (Qualtiere, L. F. and Pearson, G. R. *Virology* 102:360-369 (1980)). Antibodies binding to the Epstein-Barr virus surface protein are thought to occur in virtually everyone who is infected with Epstein-Barr virus. An assay for antibodies binding to the Epstein-Barr virus Viral Capsid Antigen (EBV-VCA) is marketed by only two manufacturers in the United States. The assay first used was manufactured by Clark Laboratories, Inc. (Jamestown, N.Y.). This firm was recently acquired by Wampole Laboratories, a division of Carter-Wallace, Inc. (Cranbury, N.J.) who has continued to provide the same viral assays. The manufacturer's instructions were followed in measuring the anti-VCA Epstein-Barr virus IgG antibodies in lupus patients and their controls, all of whom tested are under 20 years old.

The results are striking. Of the 134 tested sera from controls, 96 have IgG antibodies that bind at a sufficient level to conclude that these individuals have seroconverted. The sera from the lupus patients in this experiment are nearly all seropositive at 102 of 103 or over 99% (Table 1).

TABLE 1

Seroconversion frequencies in pediatric lupus and controls for IgG binding to Epstein Barr virus viral capsid antigen (EBV-VCA).
Anti-Epstein-Barr virus Viral Capsid Antigen IgG (#seroconverted (total tested))

| Oklahoma cases and controls | |
|---|---|
| Lupus cases | 45 (45) |
| Controls | 53 (76) |
| Odds ratio | 38 |
| $x^2$ | 15.1 |
| p | <0.0001 |
| San Diego and New York City cases and controls | |
| Lupus cases | 57 (58) |
| Controls | 43 (58) |
| Odds ratio | 20 |
| $x^2$ | 14.1 |
| p | <0.001 |
| Combined data from lupus cases and controls | |
| Lupus cases | 102 (103) |
| Controls | 96 (134) |
| Odds ratio | 40.4 |
| $x^2$ | 31.6 |
| p | <0.00000001 |

Odds ratios were calculated from the contingency tables. A $x^2$ test was used to assess significance. The assays for all viral antigens were obtained from Clark Laboratories (Jamestown, N.Y.) now a division of Wampole Laboratories (Cranberry, N.J.) and were performed according to the instructions provided by the manufacturer. The surface antigen is partially purified for the anti-Epstein-Barr virus Viral Capsid Antigen antibody assay (Qualtiere, L. F. and Pearson, G. R. *Virology* 102:360-369 (1980)).

The quantitative level of binding to the Epstein-Barr virus Viral Capsid Antigen (as measured relative to the standardized calibrator and as recommended by the manufacturer) also show substantial quantitative differences between lupus cases and controls (Table 2).

TABLE 2

Binding of IgG in sera from pediatric lupus patients and their controls to the Viral Capsid Antigen from Epstein Barr virus (EBV).
Epstein-Barr virus Viral Capsid Antigen
(International Standardized Ratios (ISRs)

| | |
|---|---|
| Lupus cases (n =103) (ISRs) | 4.368 |
| Controls (n = 134) (ISRs) | 2.087 |
| t-test | 14.82 |
| probability (p value) | <<00.001 |

Assay is performed as presented in Table 1. Data are presented as International Standardized Ratios (ISRs) which are calculated as described by the manufacturer. The average binding of each tested serum is divided by the product of the calibrator and a lot-specific factor. This allows for standardization across assays. Values considered negative and values >1.1 are considered positive. Values between 0.9 and 1.1 are equivocal and are either retested or are assigned to the not positive or negative group. (No patient serum tested to date has had a result in this equivocal range.)

If the suspected relationship between systemic lupus erythematosus held only for the lupus patients who were anti-Sm positive, then the proportion of lupus patients who had developed the anti-Epstein-Barr virus surface molecule (gp340/220) antibody would be increased over controls only modestly, since the proportion of lupus patients with anti-Sm in their sera rarely exceeds 30%. The remaining lupus patients would have been expected to have the normal control frequency of Epstein-Barr virus seroconversion.

Patients with lupus have such different clinical manifestations from patient to patient, that many investigators suspect that there are many different causes of this disease. Any given particular etiology causing lupus would then be expected to account for only a proportion of the cases. For example, assume that lupus, as observed in the clinics, happens to have two different origins, one from a virus such as Epstein-Barr virus and another from the intrinsic genetic program of some patients. Further assume that the Epstein-Barr virus only accounts for the individual patients who have anti-Sm or anti-nRNP autoantibodies and that this is half of the lupus patients (which is approximately true). Under this scenario, one would expect to see a statistical effect of increased Epstein-Barr virus infection in the group of lupus patients, as a whole, when compared to controls, but the effect would be driven by only half of the patients. Consequently, the proportion of lupus patients with evidence of Epstein-Barr virus infection would be raised, from 71% to 85.5%, but not to the 99% level that has been observed. This 99% rate is the level that would be expected if over 95% of the lupus cases in the collection have been caused by Epstein-barr virus.

The association is consistent with Epstein-Barr virus infection being a necessary condition before this autoimmune disease can develop in nearly all lupus patients. Assuming Epstein-Barr virus accounts for nearly all cases of lupus, as suggested by the data, then this virus is capable of mediating the various autoimmune manifestations found in lupus beyond just the relationship with anti-Sm antigen originally postulated. Autoantigens in lupus patients are generally thought to be found throughout the tissues of the host and not to be restricted to a single tissue. This is true for Sm, nRNP, Ro, La, P, DNA, and RNA, among many other autoantigens in lupus. Some patients may have antibodies binding other autoantigens which are tissue specific, such as thyroglobulin, but these seem to be less important in this disease. Virtually all active lupus patients have a positive antinuclear antibody, suggesting that at least one of the autoantigens bound by patient autoantibody is directed against a cellular constituent shared between tissues.

This mechanism already allows for a large number of autoantigens. If all of these autoimmune manifestations are related to Epstein-Barr virus infection, then it is probable that other autoimmune disorders are related also. Only a change in the location of the antigen in the host would be required to generate another disorder, among other mechanisms, for Epstein-Barr virus to be a necessary, but not sufficient condition for the development of other autoimmune diseases. For example, a similar mechanism could operate for thyroglobulin or thyroid peroxidase, leading to a tissue specific autoimmune disorder, autoimmune thyroid disease. Again Epstein-Barr virus infection would be a requirement before most patients could develop the disease.

Interestingly, autoimmune thyroid disease and lupus sometimes coexist in the same patient. There are those who have suspected that there is a relationship between systemic lupus erythematosus and autoimmune thyroid disease (R. H. Scofield Clin. Exp. Rheum. 14:321-330 (1996)). Under these circumstances, Epstein-Barr virus could be fundamental to both disorders. Other features of the environment, virus strain differences, genetics of the host, hormone and cytokine status, recent and remote immune history, and the nature and course of infection of the Epstein-Barr virus in the host, among other variables, probably then determine how the autoimmunity, as a consequence of Epstein-Barr virus infection, finds expression.

EXAMPLE 3

Experiments to evaluate trivial and artifactual explanations for the association of Epstein-Barr virus serologic positivity with an autoimmune disease related to the source of the test for anti-Epstein-Barr Viral Capsid Antigen IgG antibodies.

Perhaps the association observed is explained by some artefact of the manufacturing process. Since there are two manufacturers who separately prepare the Viral Capsid Antigen and who use somewhat different procedures, a subset of the lupus patients and controls were evaluated using the test manufactured by Gull Laboratories (Salt Lake City, Utah).

The results from the Gull test for Epstein-Barr seropositivity were virtually identical to those obtained with tests manufactured by Clark Laboratories, Inc. Of the 43 patient sera tested, all were positive for Epstein-Barr virus IgG antibodies who were positive by the Clark assay. The one patient without antibodies to Epstein-Barr virus Viral Capsid Antigen by the Clark assay also had no detectable antibodies to Epstein-Barr virus Viral Capsid Antigen by the Gull assay. Of the 47 control sera tested, none were negative that were previously positive and four were positive in the Gull anti-Epstein-Barr virus Viral Capsid Antigen assay that were previously negative.

This experiment established that the results in Example 1 were not explained by lot variation or an unusual property of the preparation used to detect anti-Epstein-Barr virus surface antigen.

EXAMPLE 4

Experiments to evaluate trivial and artifactual explanations for the association of Epstein-Barr virus serologic positivity with an autoimmune disease related to cross-reactivity of autoantibodies with anti-Epstein-Barr surface antigen IgG antibodies.

Next, five of the lupus patients with high levels of anti-Sm autoantibodies were arbitrarily selected. The anti-spliceosomal autoantibodies were absorbed from their sera and their antinuclear antibody titer reevaluated by immunofluorescence, and anti-Sm/nRNP and anti-Ro antibodies by solid phase assay (following previous methods (Gaither, K. K. et al. *J. Clin. Invest.* 79:841-846 (1987); Harley, J. B. et al. *Arthritis Rheum.* 29:196-206 (1986)), and anti-Epstein-Barr virus Viral Capsid Antigen IgG antibodies.

The spliceosomal antigen preparation is affinity purified from bovine tissue and contains both the Sm and nRNP specificities and, hence, is referred to as Sm/nRNP. This is the same preparation discussed herein for solid phase assays against Sm/nRNP. The previous method for the solid phase anti-Sm/nRNP assay (Gaither, K. K. et al. *J. Clin. Invest.* 79:841-846 (1987); Harley, J. B. et al. *Arthritis Rheum.* 29:196-206 (1986)) was altered by omitting inhibition with purified Sm/nRNP antigen. The same alteration was made in the anti-Ro assay.

These data show that the anti-Sm was reduced by at least 90% in each serum, as expected. In addition, the antinuclear antibodies were reduced by an average of 97%. Meanwhile, neither the anti-Ro nor the anti-Epstein-Barr virus surface antigen IgG antibodies were substantially reduced. The anti-Epstein-Barr virus surface antigen IgG antibodies were reduced by an average of 8%.

These data show that neither anti-Ro nor anti-Epstein-Barr virus Viral Capsid Antigen IgG cross-reacts to any significant extent with the anti-Sm. If they had, then these antibodies would also have been removed by the absorption. In addition, the reduction of the antinuclear antibodies in the absorbed sera by 97% suggests that the anti-Sm/nRNP is the major autoantigen in these lupus patients.

EXAMPLE 5

Experiments to evaluate trivial and artifactual explanations for the association of Epstein-Barr virus serologic positivity with an autoimmune disease related a general polyclonality of autoantibodies in lupus sera.

It was possible that lupus sera may nonspecifically bind to any viral antigen. To test this possibility, the same patient and control sera were evaluated for antibodies against four other Herpes viruses: Cytomegalovirus; Herpes simplex, type 1; Herpes simplex, Type 2; and Varicella zoster (Table 3).

TABLE 3

Seroconversion frequencies in pediatric lupus and controls for IgG binding to cytomegalovirus antigen (CMV), Herpes simplex type 1 antigen (HSV-1), Herpes simplex virus type 2 antigen (HSV-2), and varicella zoster virus (VZV) antigens.

|  | CMV | HSV-1 | HSV-2 | VZV |
|---|---|---|---|---|
| Oklahoma | | | | |
| Lupus cases | 20(45) | 30(45) | 21(45) | 42(45) |
| Controls | 21(76) | 32(76) | 22(76) | 71(76) |
| Odds ratio | 2.1 | 2.75 | 2.14 | 0.99 |
| $X^2$ | 3.57 | 6.82 | 3.84 | 0.0 |
| p | >0.05 | <0.01 | 0.05 | 0.99 |
| San Diego and New York City | | | | |
| Lupus cases | 18(58) | 33(58) | 32(58) | 46(58) |
| Controls | 12(57) | 31(57) | 23(57) | 45(57) |
| Odds ratio | 1.69 | 1.11 | 1.82 | 1.02 |
| $X^2$ | 1.49 | 0.73 | 2.53 | 0.0 |
| P | 0.22 | 0.79 | 0.11 | 0.96 |

The odds ratios were calculated from the contingency tables. A $X^2$ test was used to assess significance. The assays for all viral antigens were obtained from Clark Laboratories (Jamestown, NY) now a division of Wampole Laboratories (Cranberry, New Jersey) and were performed according to the instructions provided by the manufacturer. Whole inactivated virus is used for the CMV, HSV-1, HSV-2 and VZV antibody assays.

There is no consistent difference (at the level of p<0.05) between the controls and the lupus patients for the frequency of seroconversion against any of the viruses tested except for Epstein-Barr virus. There is a small and significant difference between the cases and controls for IgG autoantibodies against herpes simplex, Types 1 and 2 in the Oklahoma group (Table 3). Its inconsistency is typical of the results of other assays for seroconversion rates in lupus. Of these, only the difference between cases and controls for antibodies against Herpes Simplex virus Type 2 is significant across the entire collection, odds ratio is 2.07 ($X^2$=7.39, p=0.006). The low, but significant, odds ratio, suggests that the contribution of this virus is likely to be small. Some of the social behaviors that increase the risk of infection with Epstein-Barr virus probably secondarily also increase the risk of contracting Herpes Simplex virus, Type 2.

The modestly, and usually insignificantly, increased odds ratios for the seroprevalence of cytomegalovirus and Herpes simplex Types 1 and 2 in lupus patients compared to controls may reflect the increased levels of binding of antibodies found in other studies (Hollinger, F. B. et al. *Bact. Proc.* 131:174 (1970); Phillips, P. E. and Christian, C. L. *Science* 168:982-4 (1970); Hurd, E. R. et al. *Arthritis Rheum.* 13:724-33 (1970)).

In conclusion, these control assays do not support the position that the difference in the seroconversion rate between lupus patients and their collected controls is the result of a nonspecific binding to viral antigens.

EXAMPLE 6

Experiments to evaluate trivial and artifactual explanations for the association of Epstein-Barr virus serologic positivity with an autoimmune disease related to hypergammaglobulinemia in the sera of patients with autoimmune disease.

To determine whether hypergammaglobulinemia might explain the differences observed, the IgG level in 32 of the lupus patients was assayed and compared this with the level found in 25 controls. No significant difference was found. In addition, no correlation was found between the IgG level and positive Epstein-Barr virus Viral Capsid Antigen assays. Therefore, an increased level of IgG binding non-specifically to the Epstein-Barr virus Viral Capsid Antigen cannot be an explanation for the findings.

EXAMPLE 7

Demonstration of an increased rate of Epstein-Barr virus infection in systemic lupus erythematosus.

An assay for Epstein-Barr virus infection that is not dependent upon serologic analysis removes all of the technical reservations concerning possible artefact or a trivial explanation for the observed association between seroconversion against Epstein-Barr virus Viral Capsid Antigen and an autoimmune disease. To assay for Epstein-Barr virus, independent of serology, a method altered from the DNA based assays already available was developed. The BamHI W repeat nucleic acid sequence of the Epstein-Barr virus genome contains a sequence repeated 11 times that others have used to detect the virus (Saito et al., *J. Exp. Med.* 169:2191-2198, 1989; and Miyashita et al., *Cell* 80:593-601, 1995). These assays were evaluated in an effort to increase specificity. Two mcg DNA specimens were isolated from peripheral blood mononuclear cells. Quantitation of DNA was based both upon optical density measurements at 240 and 260 nm and quantitation of ethidium bromide fluorescence in agarose gel relative to known DNA standards. Where available, six reactions, each containing 2 mcg of mononuclear cell DNA, were evaluated from each subject. The primers and the probe used are given in Table 4.

TABLE 4

Primers and probe used to expand Epstein-Barr virus DNA from the BamHI W repeat.

| | |
|---|---|
| Forward - | 5'-CCAGAGGTAAGTGGACTT-3',(SEQ ID NO: 10) |
| Reverse - | 5'-GACCGGTGCCTTCTTAGG-3' (SEQ ID NO: 11) |
| Probe - | 5'-AAGACGATTCGGGTTG (TGAGGTGGTGTGGGTCCG-TGTGTGATGTGTGTGGGTGGGCAG)*-3' (SEQ ID NO: 12) |

*The $^{32}$P-dCTP label is incorporated into the portion of the sequence in parentheses.

The polymerase chain reaction for each DNA specimen was run in a final volume of 75 mcl with 50 mM KCl, 10 mM Tris-HCl at pH 8.0, 1.5 mM $MgCl^2$, 0.1% Triton X-100, 0.2 mM each dNTP, 0.5 mcM primer, and 2.5 U Taq DNA polymerase. A hot start protocol was followed using Ampliwax PCR Gems™ (Perkin-Elmer, Branchburg, N.J.). The thermocycler was programmed for the following temperature cycles: (95° C. for 2 min, 57° C. for 1 min, 72° C. for 1 min) twice, (94° C. for 1 min, 55° C. for 1 min, 72° C. for 45 sec) 31 times, 72° C. for 5 min.

The primers variably expanded four bands from found at approximately 92, 122, ~500, and ~700 base pairs. All four were cloned into the pCRII vector (Invitrogen, San Diego, Calif.) and at least partially sequenced. The 92, ~500, and ~700 base pair products of the polymerase chain reaction are not in the GeneBank database. They are likely to represent human sequence from a region of the genome that has not yet been sequenced.

The 122 base pair product was similarly cloned and sequenced. The sequence obtained exactly matched the sequence predicted from the Epstein-Barr virus BamHI W repeat, which is repeated 11 times and found at positions 14614-14735, 17686-17807, 20758-20879, 23830-23951, 26902-27023, 29974-30095, 33046-33167, 36118-36239, 39190-39311, 42262-42383, and 45334-45455 of the Epstein-Barr DNA sequence (GenBank accession number: v01555). Only this product of the polymerase chain reaction, found at 122 base pairs, hybridized to the radiolabled probe.

The existing assays for Epstein-Barr DNA were modified so that the assay applied would be as sensitive and specific as the serologic assays are for infection in normal individuals. To achieve this goal a total of 12 mcg of mononuclear DNA in six polymerase chain reactions were evaluated. A long probe was used so that very small amounts of expanded BamHl W fragment DNA can be detected.

This assay was used in 50 subjects. Of these, 38 individuals that had positive Epstein-Barr virus Viral Capsid Antigen ("EBV-VCA") IgG antibodies (as determined by the assay from Clark Laboratories, Inc.) also expanded the predicted 122 base pair DNA fragment which hybridized to the BamHI W probe from the Epstein-Barr viral DNA sequence. Epstein-Barr virus DNA was recovered in three other subjects whose serologic assays were not positive. In one of these subjects the serologic results for Epstein-Barr virus Viral Capsid Antigen IgG was close to the positive range, as determined in comparison to the calibrator sera provided by the manufacturer. One control had evidence of antibodies to EBV-VCA but no evidence of EBV-DNA as determined by the method described herein. Neither anti-Epstein-Barr virus Viral Capsid Antigen IgG antibodies nor Epstein-Barr virus DNA was detected in the other seven subjects tested.

The new assay has high sensitivity and specificity relative to the serologic analysis. Actually, the direct detection of viral DNA, if true, is a more proximal indication of infection than is seroconversion and is probably a better standard for viral infection than is serology.

The detection of Epstein-Barr virus DNA has proven to be sufficiently reliable for application to the evaluation of the frequency of Epstein-Barr virus infection in lupus and their controls. A matched case-control design was followed. Cases of lupus in children and adolescents (<20 years old) had been enrolled into this experiment as they were encountered along with a sex, age (within two years), and race matched control. To control for socioeconomic factors and likelihood of viral exposure, each case was asked to provide a relative or fiend to serve as a control. Relatives were preferred over friends. The inventors selected controls for eight cases who did not provide their own control.

The data were evaluated with the Exact Binomial Test for Matched Data. Of the 25 lupus cases, all 25 had been infected by Epstein-Barr virus as determined by the assay for viral DNA and also had antibodies directed against Epstein-Barr Viral Capsid Antigen. Of the 25 matched controls, 17 had been infected by Epstein-Barr virus as determined by the assay for viral DNA. Of the 17 with viral DNA, 14 had IgG antibodies directed against Epstein-Barr virus Viral Capsid Antigen and three did not. One control had no detectable DNA from the virus by the assay and yet had anti-Epstein-Barr virus Viral Capsid Antigen IgG antibodies.

To evaluate these data from the most conservative perspective, subjects were required to be negative in both assays in order to conclude that a particular subject had not been infected with Epstein-Barr virus. By these criteria seven of the matched pairs were discordant for infection. All seven of these discordant pairs are discordant in the same way, Epstein-Barr virus infection had occurred in the case and not in the control, which is very unlikely to have occurred by chance (p<0.008) (Table 5).

TABLE 5

Matched case-control evaluation of the presence of Epstein-Barr DNA in peripheral blood mononuclear cells from lupus patients (cases) and controls matched for sex, race, and age (+/− 2 years).

| Epstein-Barr virus infection | | |
|---|---|---|
| Lupus Cases | Matched Control | |
| + | + | 18 |
| + | − | 7 |

TABLE 5-continued

Matched case-control evaluation of the presence of
Epstein-Barr DNA in peripheral blood mononuclear cells
from lupus patients (cases) and controls matched for
sex, race, and age (+/− 2 years).

| - | + | 0 |
|---|---|---|
| - | - | 0 |

The probability of this distribution occurring by chance is p=0.0078 by the Exact Binomial Test for Matched Data. The odds ratio for this distribution cannot be calculated because of the zero cell. If the usual adjustment of 0.5 is made then the odds ratio is estimated to be =\>13.

These results dramatically confirm the serologic data. Collectively, these data, the serologic results and the control experiments establish that there is a virtually complete association of Epstein-Barr virus infection with systemic lupus erythematosus.

EXAMPLE 8

Antibodies against some Epstein-Barr virus structures are associated with the presence of an autoimmune disease, compositions for diagnostics.

Figure 3:
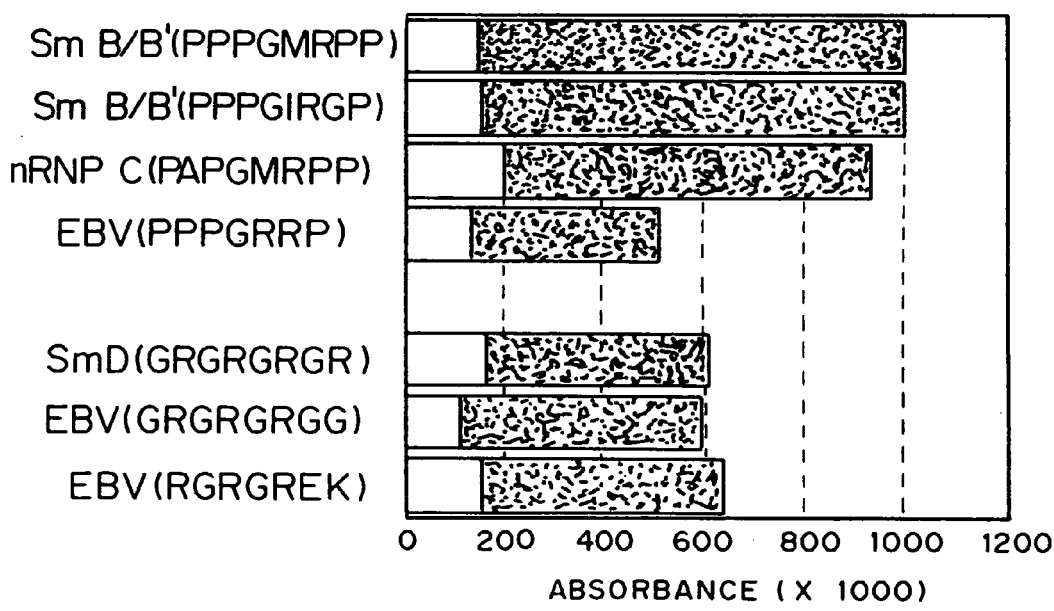
FIG. 3 is a graph of binding to selected peptides from the B/B', C and D spliceosomal proteins and from Epstein-Barr virus nuclear antigen-1 proteins (PPPGRRP (SEQ ID NO:1), GRGRGRGG (SEQ ID NO:2), and RGRGREK (SEQ ID NO:3)) in six lupus patient sera (which are anti-Sm and anti-nRNP precipitin positive) (black) and five control sera (shown overlaid in white). The peptides shown are, in order, SEQ ID NO:4, SEQ ID NO:5, SEQ ID NO:6, SEQ ID NO:1, amino acids 1 to 8 of SEQ ID NO:9, SEQ ID NO:2, and SEQ ID NO:3.
Figure 4A:
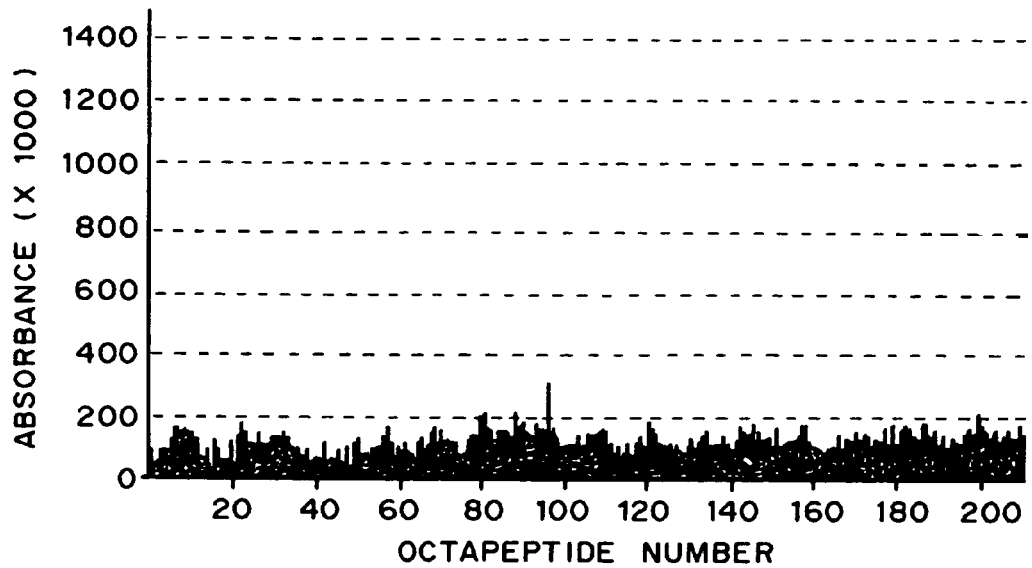
FIGS. 4A-D are graphs of the development of an anti-Sm B/B' response in one anti-Sm and anti-nRNP precipitin positive patient. Binding to 211 octapeptides of Sm B/B' is presented as absorbance (X 1000) at 405 nm.
Figure 4B:
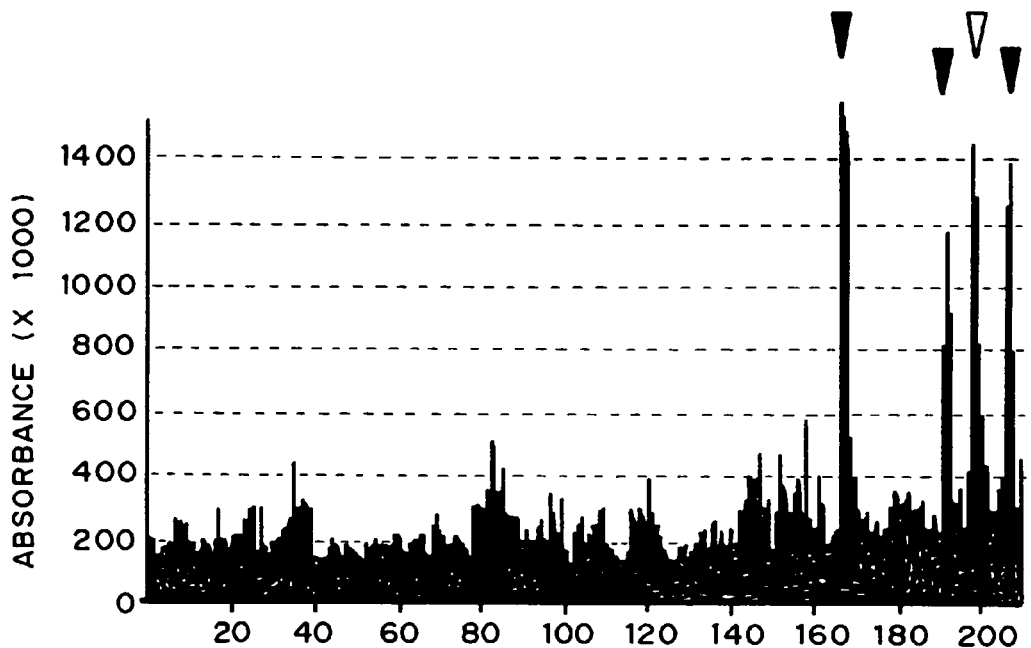
Figure 4C:
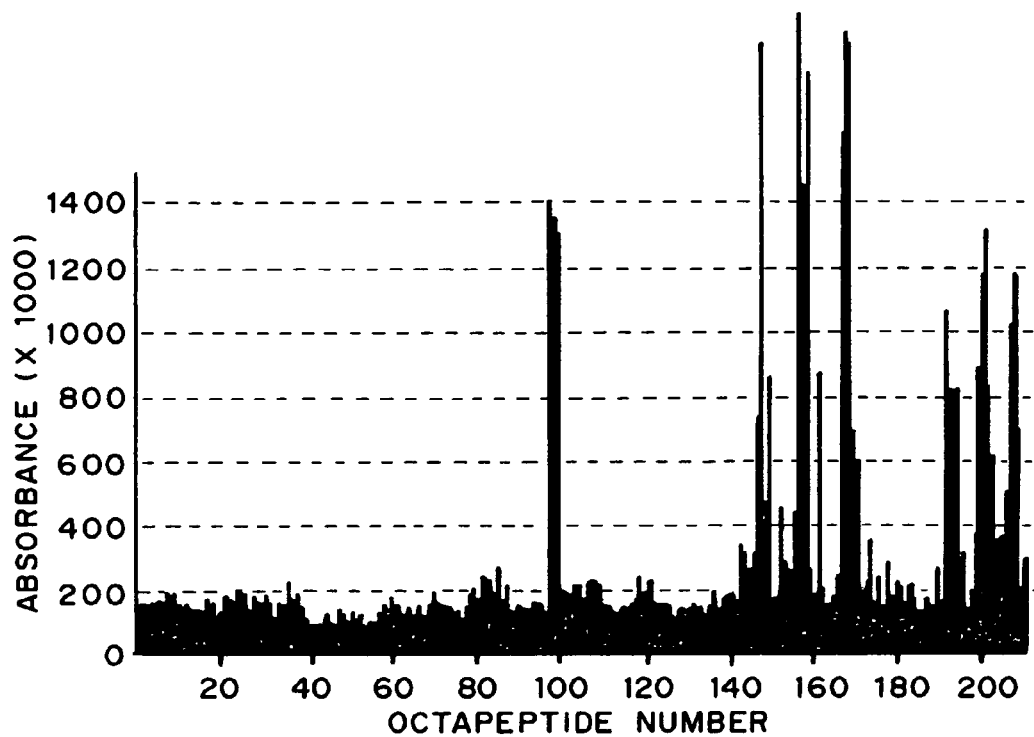
Figure 4D:
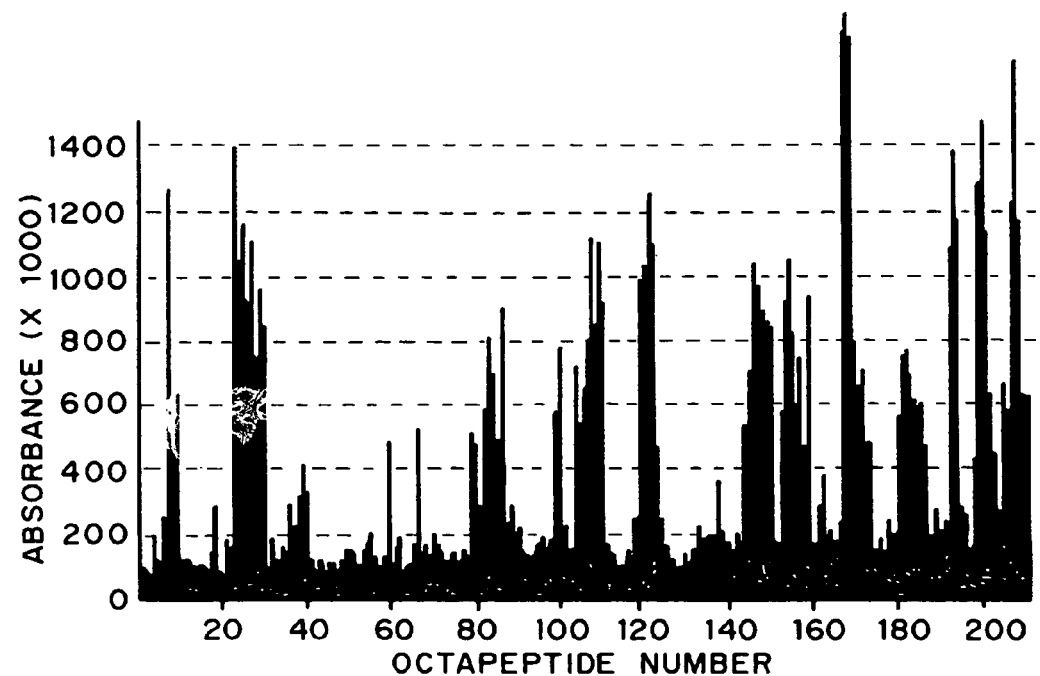
Figure 6A:
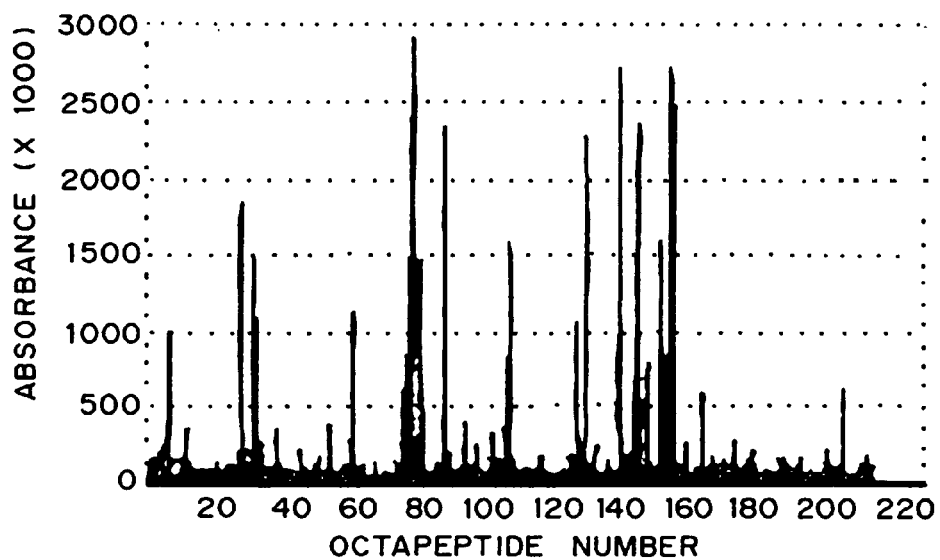
FIGS. 6A-D are graphs of the binding of two rabbit sera to the overlapping octapeptides of the spliceosomal proteins B/B' (FIGS. 6A and 6C) and D (FIGS. 6B and 6D). The two rabbits (numbers 40 and 41) were immunized with PPPGRRP-MAP™ (SEQ ID NO:1) 86 days earlier. The serum in FIGS. 5A and 5B binds to nRNP/Sm, and is positive in the antinuclear antibody assay and the anti-double stranded DNA assay (*Crithidia lucilea* kinetoplast fluorescence assay) while the serum from the second rabbit was not positive in any of these other assays.
Figure 6B:
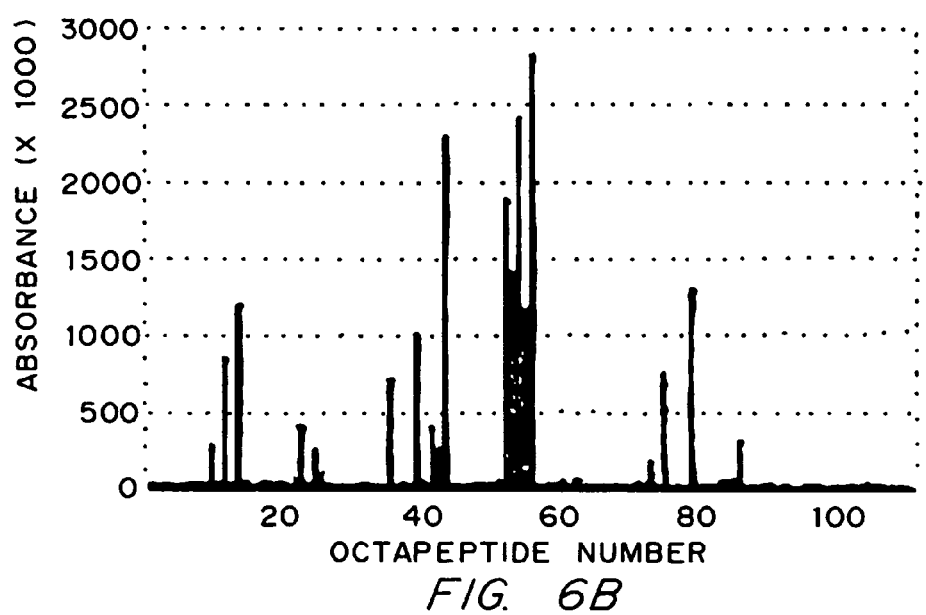
Figure 6C:
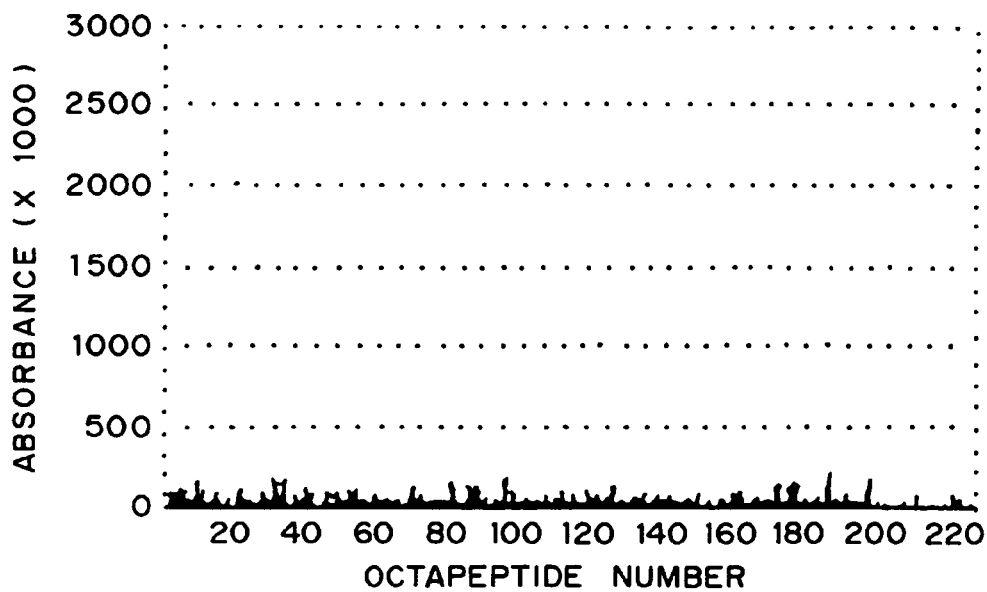
Figure 6D:
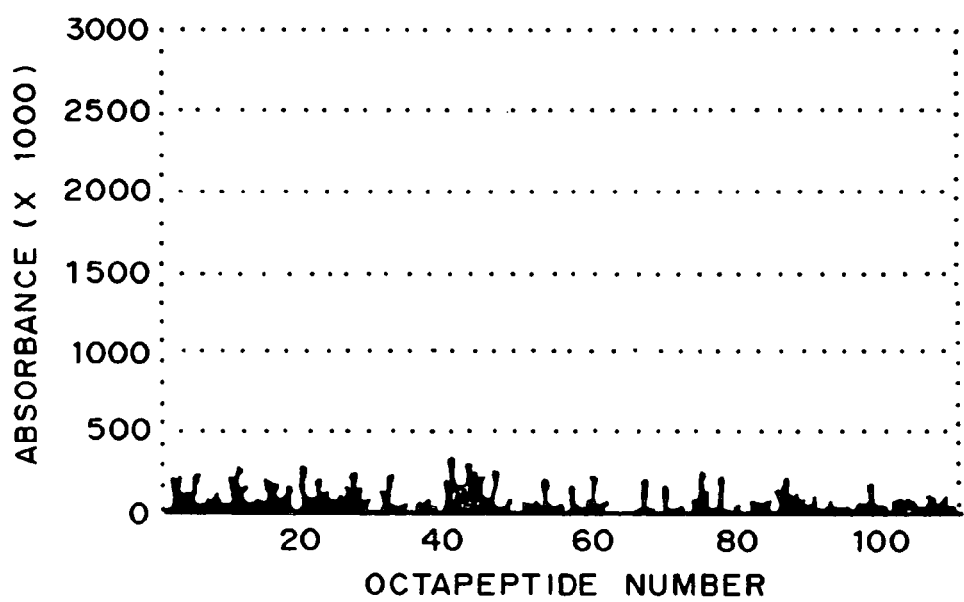
Figure 7:
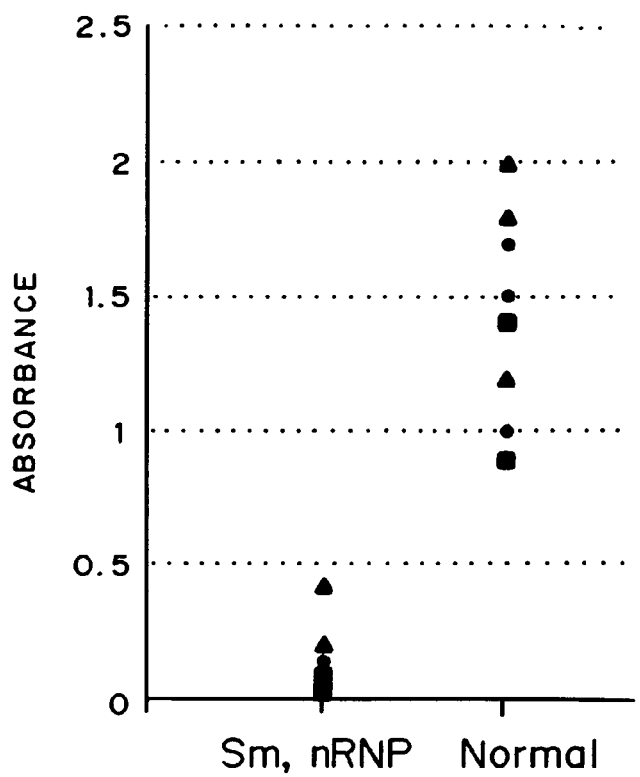
FIG. 7 is a graph of the binding to the peptide GAGAGAGAGAGAGAGAGAGAGAGAGA (SEQ ID NO:7) from Epstein-Barr virus Nuclear Antigen-1 by lupus sera who all had anti-Sm and anti-nRNP precipitins, as compared to normal control sera.

Four peptide sequences from Epstein-Barr virus were separately evaluated for binding to sera from patients with an autoimmune disease (FIGS. 3 and 7). All are found in the EBNA-1 (Epstein-Barr virus Nuclear Antigen-1) protein. Subjects with an autoimmune disease, systemic lupus erythematosus, tend to have higher levels of antibodies against PPPGRRP (SEQ ID NO:1), GRGRGRGG (SEQ ID NO:2) and RGRGREK (SEQ ID NO:3) than do normal controls. On the other hand the glycine-alanine repeat sequence, GAGAGAGAGAGAGAGAGAGAGAGA (SEQ ID NO:7) which, after infection by Epstein-Barr virus, is a major epitope in infectious mononucleosis and in normals (Rhodes, G. et al. *J. Exp. Med.* 165:1026-1040 (1987)) tends not to be bound by patients with lupus (FIG. 7).

The overlapping octapeptides were constructed from the sequence of EBNA-1 (Epstein-Barr virus Nuclear Antigen-1) protein and preliminarily evaluated in four lupus patient sera and four controls. One control had no serologic evidence of having been exposed to Epstein-Barr virus, while the other three have anti-Epstein-Barr virus Viral Capsid Antigen IgG antibodies. All four of the patients had anti-Epstein-Barr virus Viral Capsid Antigen IgG antibodies.

The binding to octapeptides from EBNA-1 (Epstein-Barr virus Nuclear Antigen-1) protein shows dramatically different patterns between the Epstein-Barr virus exposed lupus patients and normal controls (FIG. 8). These and other differences could become the basis for diagnostics that predict the risk of an autoimmune disease, that are associated with the presence of an autoimmune disease, and that are associated with particular clinical findings or manifestations. The structures bound by the lupus sera tested are listed in Table 6.

TABLE 6

Octapeptides from Epstein-Barr virus Nuclear Antigen-1
bound by the sera from two patients with systemic lupus
erythematosus.

| Octapeptide Number | Sequence | Vaughan |
|---|---|---|
| 30-48 | GPQRRGGDNHGRGRGRGRGRGGGRPG (SEQ ID NO:13) | |
| 58-70 | GGSGSGPRHRDGVRRPQKRP (SEQ ID NO:14) | |

TABLE 6-continued

Octapeptides from Epstein-Barr virus Nuclear Antigen-1
bound by the sera from two patients with systemic lupus
erythematosus.

| Octapeptide Number | Sequence | Vaughan |
|---|---|---|
| 72 | RPQKRPSC (SEQ ID NO:15) | |
| 74-83 | QKRPSCIGCKGTHGGTG | |
| 88-93 | GTGAGAGARGRGG | |
| 334 | SGGRGRGG | e1* |
| 347-351 | RGGSGGRRGRGR | |
| 368-376 | RARGRGRGRGEKRPRS | e4* |
| 388-394 | SSSSGSRRPPPGR | |
| 397-414 | RPPPGRRPFFHPVGEADYFEYHQEG | |
| 427 | PDVPPGAI (SEQ ID NO:23) | |
| 431 | PGAIEQGPA (SEQ ID NO:24) | |
| 445 | GPSTGPRG (SEQ ID NO:25) | |
| 452-453 | GQGDGGRRK (SEQ ID NO:26) | e14* |
| 455-462 | DGGRRKKGGWFGKHR (SEQ ID NO:27) | e14* |
| 466-468 | GKHRGQGGSN (SEQ ID NO:28) | e11* |
| 470 | GQGGSNPK (SEQ ID NO:29) | |
| 475 | NPKFENIA (SEQ ID NO:30) | |
| 491 | RSHVERTT (SEQ ID NO:31) | |
| 508 | VFVYGGSKT (SEQ ID NO:32) | |
| 512-513 | GSKTSLYNL (SEQ ID NO:33) | |
| 542 | GMAPGPGP (SEQ ID NO:34) | e12* |
| 549 | PQPGPLRE (SEQ ID NO:35) | |
| 591 | CNIRVTVC (SEQ ID NO:36) | |
| 594-596 | RVTVCSFDDG (SEQ ID NO:37) | |
| 607-608 | PPWFPPMVEG (SEQ ID NO:38) | e10* |

Figure 8A:
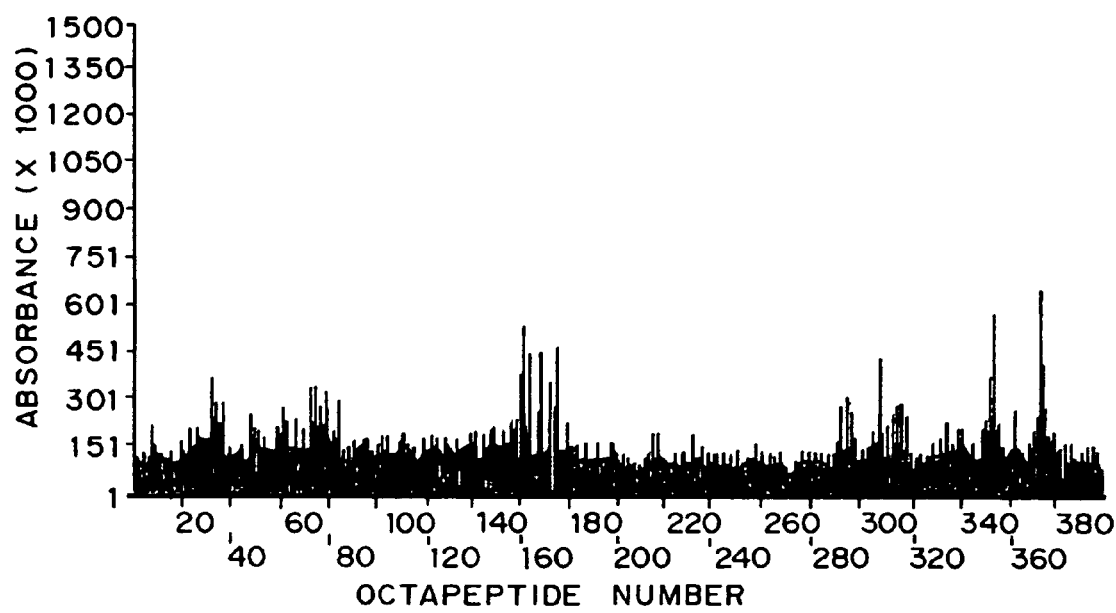
FIGS. 8A-E are graphs of the binding to the overlapping octapeptides from Epstein-Barr virus Nuclear Antigen-1. Each octapeptide overlaps its neighbor by seven amino acids. Most of the glycine-alanine repeat has been omitted to avoid unnecessary redundancy. The binding of three controls are presented in FIGS. 8A, 8B and 8C and that of two lupus sera in FIGS. 8D and 8E.
Figure 8B:
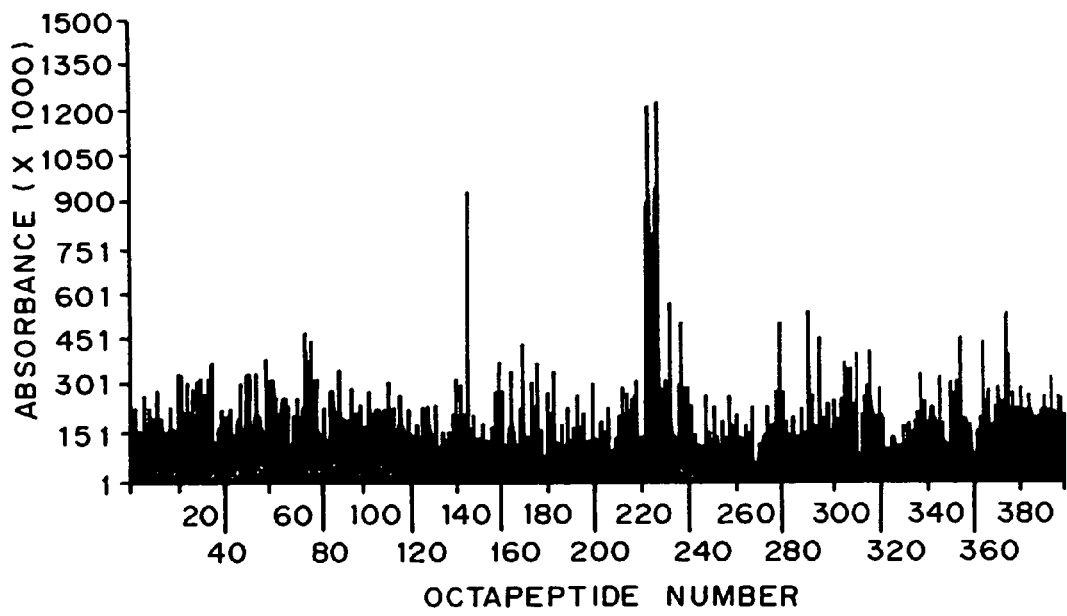
Figure 8C:
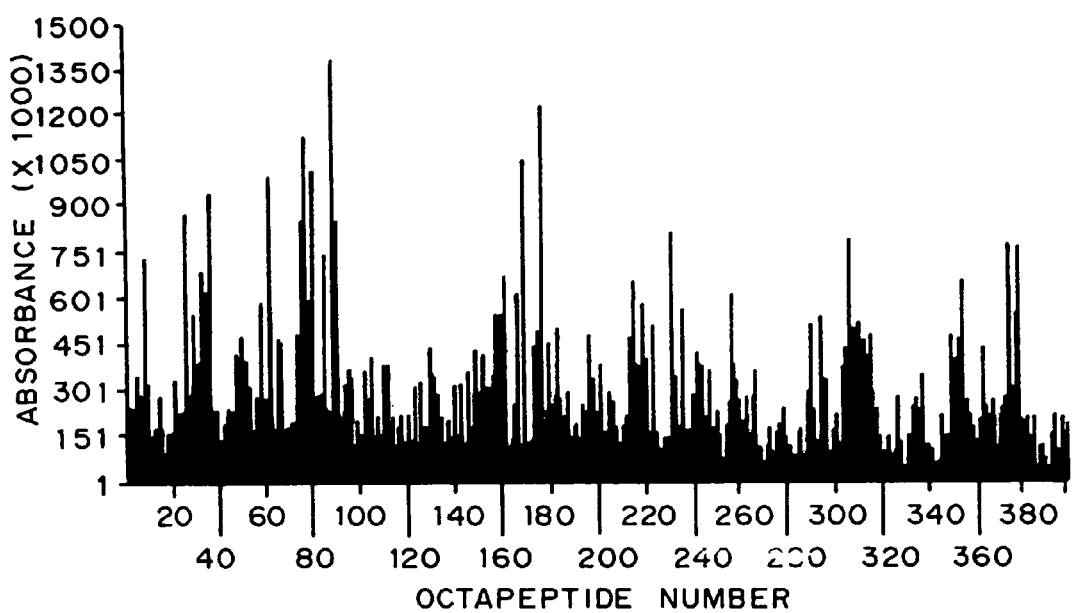
Figure 8D:
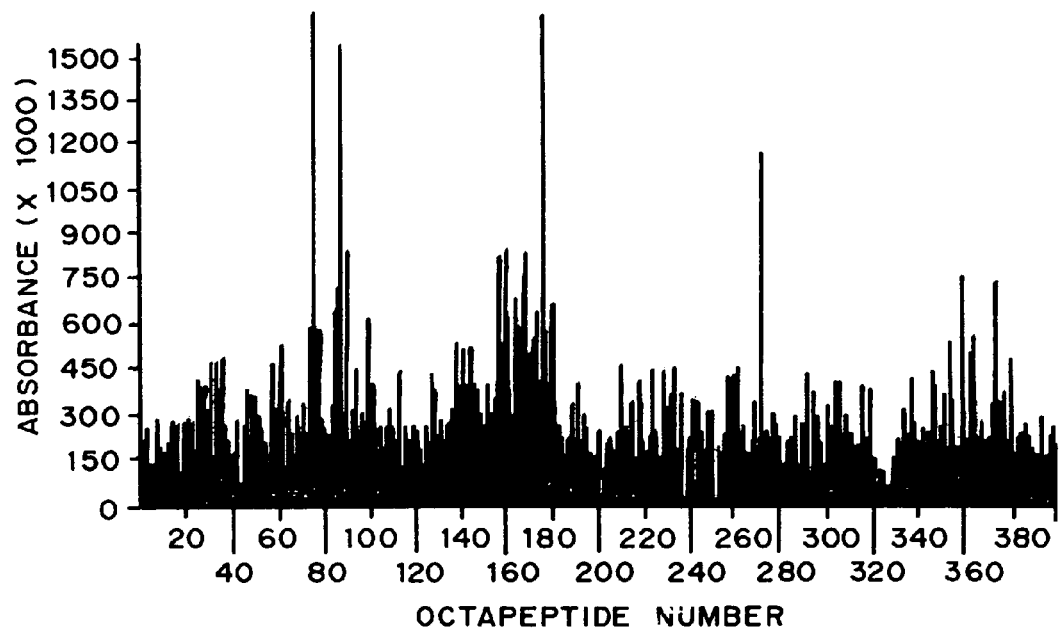
Figure 8E:
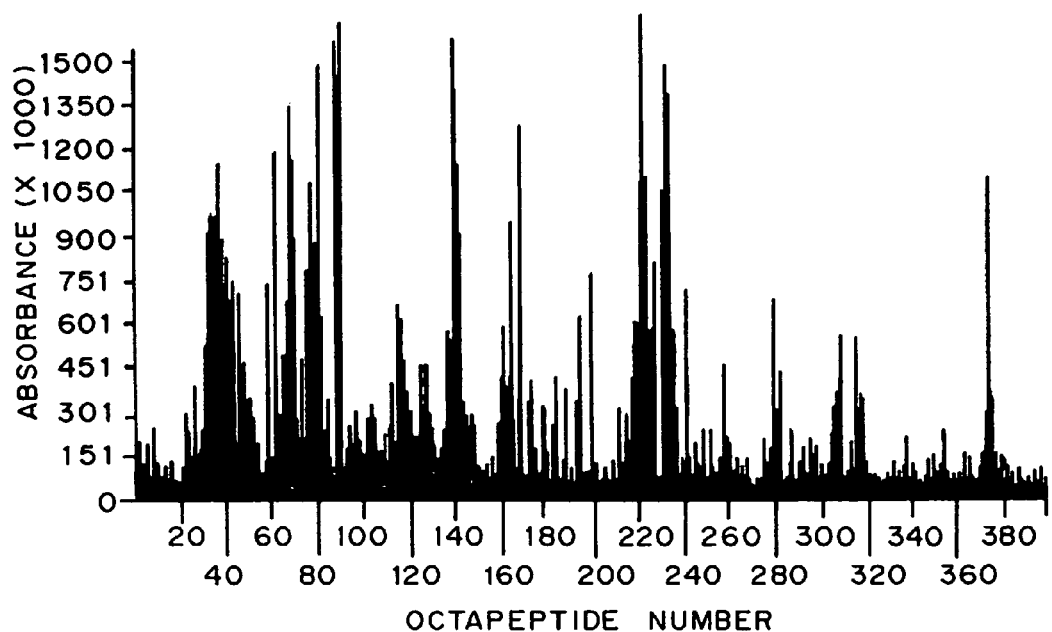

These are taken from the data in FIGS. 8D and 8E. The peptides presented were bound in one of the sera by greater than 0.450 Absorbance Units. Sequences longer than eight amino acids represent neighboring octapeptides that exceed the 0.450 A.U. threshold. Studies by John Vaughan and colleagues found some peptides of Epstein-Barr virus Nuclear Antigen-1 to be more antigenic in lupus patients than in controls (Petersen, et al, *Arthritis Rheum.* 33: 993-1000 (1990)). The octapeptides which share sequence with the peptides that were used in the Peterson study are identified with the peptide name used in their study (Table 6). Those peptides which they found to be differentially bound by lupus sera, relative to control sera, are identified with an *.

Other differences in the antibody and cellular responses are expected to be important for the purpose of predicting the presence of (diagnosis) or subsequent risk of an autoimmune disease. Those presented above are examples of structures potentially useful for this purpose.

Assuming Epstein-Barr virus causes some autoimmune diseases, then differences in the immune response against this virus have the potential to predict risk of autoimmune disease and to be an aid to diagnosis and management of autoimmune disease.

Other structures defined by the proteins, glycoproteins nucleic acids, etc., will also be useful for this purpose. Such diagnostic tests can be based upon the relative presence of an antibody, cellular proliferation, molecular binding, cytokine production, skin reaction (erythema or induration), cell surface antigen or other measure of activation.

EXAMPLE 9

Use of a vaccine composition designed to induce a response to prevent or treat an autoimmune disease.

Assuming Epstein-Barr virus causes autoimmune disease, then an effective vaccine which induces a protective response against Epstein-Barr virus has the potential to protect the host from the autoimmune disease. This is particularly true if the structure(s) which induce autoimmune disease is(are) altered or removed from the vaccine.

Once infected, this virus is latent and in most, perhaps virtually all, individuals the virus emerges from latency at a low level throughout the remainder of life. The viral infected cells or the immune response required to suppress the virus have the potential to be extremely important in inducing or sustaining the autoimmune disease. Cells latently infected by Epstein-barr virus may also alter the immune response. Consequently, treatments designed to suppress or eliminate Epstein-Barr virus have the potential to ameliorate the symptoms and tissue damage of the autoimmune disease.

Treatments expected to be useful against autoimmune disease include compositions that suppress the emergence of Epstein-Barr virus from latency. Also, agents for gene therapy directed against Epstein-Barr virus will be useful. Biologicals may also prove useful against Epstein-Barr virus by altering the intracellular environment, making it less hospitable to the virus by directly affecting the virus or by making the immune response against the virus less prone to support an autoimmune disease process.

Modification and variations of the methods and composition of the present invention will be obvious to those skilled in the art from the foregoing detailed description of the invention. Such modifications and variations are intended to come within the scope of the following claims.

We claim:

1. A peptide composition comprising a peptide molecule consisting of about forty amino acids or less and comprising a peptide sequence selected from the group consisting of PPPGRRP (SEQ ID NO:1), GRGRGRGG (SEQ ID NO:2), RGRGREK (SEQ ID NO:3), GPQRRGGDNHGRGRGRGRGRGGGRPG (SEQ ID NO:13), GGSGSGPRHRDGVRRPQKRP (SEQ ID NO:14), GTGAGAGARGRGG (SEQ ID NO:17), SGGRGRGG (SEQ ID NO:18), RGGSGGRRGRGR (SEQ ID NO:19), SSSSGSPPRRPPPGR (SEQ ID NO:21), RPPPGRRPFFHPVGEADYFEYHQEG (SEQ ID NO:22), GPSTGRPG (SEQ ID NO:25), GQGDGGRRK (SEQ ID NO:26), DGGRRKKGGWFGKHR (SEQ ID NO:27), GKHRGQGGSN (SEQ ID NO:28), GQGGSNPK (SEQ ID NO:29), NPKFENIA (SEQ ID NO:30), RSHVERTT (SEQ ID NO:31), VFVYGGSKT (SEQ ID NO:32), GSKTSLYNL (SEQ ID NO:33), CNIRVTVC (SEQ ID NO:36), PPWFPPMVEG (SEQ ID NO:38) and combinations thereof, wherein the peptide is present either in free form or bound to a carrier molecule.

2. The composition of claim 1, wherein the peptide molecule or molecules are in a pharmaceutically acceptable carrier.

3. The composition of claim 1 mobilized to a solid support.

4. The composition of claim 3 immobilized to multiwell plates.

5. The composition of claim 3 immobilized to a gel suitable for affinity chromatography.

6. The composition of claim 1 labeled with a detectable label.

7. The composition of claim 1 bound by autoantibodies in patients characterized by specific disorders.

8. A method for determining the likelihood that an individual has or will develop an autoimmune disorder comprising screening their antibodies for reactivity with a peptide molecule consisting of about forty amino acids or less and comprising a peptide sequence selected from the group consisting of PPPGRRP (SEQ ID NO:1), GRGRGRGG (SEQ ID NO:2), RGRGREK (SEQ ID NO:3), GAGAGAGAGAGAGAGAGAGAGAGA (SEQ ID NO:7), GPQRRGGDNHGRGRGRGRGRGGGRPG (SEQ ID NO:13), GGSGSGPRHRDGVRRPQKRP (SEQ ID NO:14), RPQKRPSC (SEQ ID NO:15), QKRPSCIGCKGTHGGTG (SEQ ID NO:16), GTGAGAGARGRGG (SEQ ID NO:17), SGGRGRGG (SEQ ID NO:18), RGGSGGRRGRGR (SEQ ID NO:19), RARGRGRGRGEKRPRS (SEQ ID NO:20), SSSSGSPPRRPPPGR (SEQ ID NO:21), RPPPGRRPFFHPVGEADYFEYHQEG (SEQ ID NO:22), GPSTGRPG (SEQ ID NO:25), GQGDGGRRK (SEQ ID NO:26), DGGRRKKGGWFGKHR (SEQ ID NO:27), GKHRGQGGSN (SEQ ID NO:28), GQGGSNPK (SEQ ID NO:29), NPKFENIA (SEQ ID NO:30), RSHVERTT (SEQ ID NO:31), VFVYGGSKT (SEQ ID NO:32), GSKTSLYNL (SEQ ID NO:33), GMAPGPGP (SEQ ID NO:34), PQPGPLRE (SEQ ID NO:35), CNIRVTVC (SEQ ID NO:36), RVTVCSFDDG (SEQ ID NO:37), PPWFPPMVEG (SEQ ID NO:38) and combinations thereof, wherein the peptide is present in either free form or bound to a carrier molecule.

9. The method of claim 8 wherein the peptide molecules are immobilized to a solid support.

10. The method of claim 8 wherein the peptide molecules are labeled with a detectable label.

11. The method of claim 8 wherein the peptide molecules are immoblized to multiwell plates.

12. The method of claim 8 wherein the peptide molecules are immobilized to a gel suitable for affinity chromatography.

13. The method of claim 8 wherein the peptide molecules are bound by autoantibodies.

* * * * *